United States Patent
McDaid et al.

(10) Patent No.: US 11,826,359 B2
(45) Date of Patent: Nov. 28, 2023

(54) PEDIATRIC SUSPENSION FORMULATION

(71) Applicant: Xeolas Pharmaceuticals Ltd., Dublin (IE)

(72) Inventors: Dennis Mark McDaid, Dublin (IE); Damien Patrick Flynn, Dublin (IE); Maurice Joseph Anthony Clancy, Dublin (IE)

(73) Assignee: Xeolas Pharmaceuticals Ltd., Dublin (IE)

( * ) Notice: Subject to any disclaimer, the term of this patent is extended or adjusted under 35 U.S.C. 154(b) by 0 days.

(21) Appl. No.: 17/061,630

(22) Filed: Oct. 2, 2020

(65) Prior Publication Data

US 2021/0100784 A1    Apr. 8, 2021

Related U.S. Application Data

(60) Provisional application No. 63/062,785, filed on Aug. 7, 2020, provisional application No. 62/911,689, filed
(Continued)

(51) Int. Cl.
*A61K 31/4439* (2006.01)
*A61J 1/00* (2023.01)
(Continued)

(52) U.S. Cl.
CPC ............. *A61K 31/4439* (2013.01); *A61J 1/00* (2013.01); *A61K 9/0053* (2013.01);
(Continued)

(58) Field of Classification Search
CPC .............. A61K 31/4439; A61K 9/0053; A61K 9/1652; A61K 47/02
See application file for complete search history.

(56) References Cited

U.S. PATENT DOCUMENTS 5,840,737 A    11/1998    Phillips
8,093,271 B2    1/2012    Los
(Continued)

FOREIGN PATENT DOCUMENTS

EP    2201952 A1    6/2010
EP    1905426 B1    9/2012
(Continued)

OTHER PUBLICATIONS

DellaGreca et al., Chemosphere, 2006;63:1087-1093 (Year: 2006).*
(Continued)

*Primary Examiner* — San Ming R Hui
(74) *Attorney, Agent, or Firm* — STERNE, KESSLER, GOLDSTEIN & FOX P.L.L.C.

(57) ABSTRACT

The present disclosure relates to storage-stable proton pump inhibitor (PPI) systems comprising a therapeutically effective amount of a PPI or a pharmaceutically acceptable salt thereof, such as omeprazole or a pharmaceutically acceptable salt thereof, which are constituted with water prior to administration. The present disclosure also relates to oral pharmaceutical suspensions comprising water, a therapeutically effective amount of a PPI or a pharmaceutically acceptable salt thereof, such as omeprazole or a pharmaceutically acceptable salt thereof, and one or more buffering agents.

27 Claims, 1 Drawing Sheet

← PICS Cap containing drug loaded powder:
- Omeprazole
- Sodium hydrogen carbonate
- Sodium alginate
- Mannitol ← Bottle containing diluent powder:
- Sodium hydrogen carbonate
- Potassium hydrogen carbonate
- Sodium alginate
- Mannitol
- Sucralose
- Xanthan gum
- Sodium benzoate
- Methyl paraben sodium
- Maltitol
- Titanium dioxide
- Flavouring(s)

Related U.S. Application Data on Oct. 7, 2019, provisional application No. 62/911,035, filed on Oct. 4, 2019.

(51) Int. Cl.

| | | |
|---|---|---|
| *A61K 9/00* | (2006.01) | |
| *A61K 47/36* | (2006.01) | |
| *A61K 47/02* | (2006.01) | |
| *A61K 47/14* | (2017.01) | |
| *A61K 47/26* | (2006.01) | |
| *A61K 9/16* | (2006.01) | |

(52) U.S. Cl.
CPC ............ *A61K 9/1652* (2013.01); *A61K 47/02* (2013.01); *A61K 47/14* (2013.01); *A61K 47/26* (2013.01); *A61K 47/36* (2013.01)

(56) References Cited

U.S. PATENT DOCUMENTS

| | | | |
|---|---|---|---|
| 9,051,100 B2 | 6/2015 | Suzuki | |
| 9,351,966 B2 | 5/2016 | Phillips | |
| 10,238,803 B2 | 3/2019 | Kumar et al. | |
| 10,285,908 B2 | 5/2019 | Mittal et al. | |
| 11,207,307 B2 | 12/2021 | Fallin et al. | |
| 2005/0098526 A1* | 5/2005 | Catalin .............. | B65D 21/0231 215/6 |
| 2005/0220870 A1* | 10/2005 | Hepburn ................ | A61K 47/02 424/464 |
| 2005/0249806 A1 | 11/2005 | Proehl et al. | |
| 2012/0142737 A1 | 6/2012 | Taneja et al. | |
| 2014/0271853 A1 | 9/2014 | Hall et al. | |
| 2014/0311929 A1 | 10/2014 | Tickle et al. | |
| 2015/0011588 A1 | 1/2015 | Hepburn et al. | |
| 2018/0042901 A1 | 2/2018 | Sutherland et al. | |

FOREIGN PATENT DOCUMENTS

| | | |
|---|---|---|
| ES | 2283172 A1 | 10/2007 |
| GB | 2189698 A | 11/1987 |
| WO | WO-200151050 A1 | 7/2001 |
| WO | WO-2008016887 A2 | 2/2008 |
| WO | WO-2013139377 A1 | 9/2013 |
| WO | WO-2017218894 A1 | 12/2017 |

OTHER PUBLICATIONS

International Search Report and Written Opinion for International Application No. PCT/IB2020/059280, European Patent Office, Netherlands, dated Jan. 19, 2021, 18 pages.

EPO machine translation of ES 2281172 A1 (document FP1), European Patent Office, Netherlands, dated Jan. 13, 2021, 12 pages.

Allison, M.E. and Walker, V., "The sodium and potassium intake of 3 to 5 year olds," Arch. Dis. Child. 61(2):159-163, BMJ, United Kingdom (1986).

Dettmar, P.W., et al., "Administration of alginate based gastric reflux suppressant on the bioavailability of omeprazole," GI Café 7(2): p. 1, Square Pharmaceuticals Ltd., Bangladesh (2014) (total 4 pages).

Higuera-De-La-Tijera, F., "Efficacy of omeprazole/sodium biocarbonate treatment in gastroesophageal reflux disease: a systematic review," MedWave 18(1):e719, Medwae Estudios Limitada, Chile (2018) (7 pages).

Leiman, D.A., et al., "Alginate therapy is effective treatment for GERD symptoms: a systematic review and meta-analysis," Dis. Esophag. 30(5):1-9, Oxford Academic Press, United Kingdom (2017).

Manabe, N., et al., "Effiicacy of adding sodium alginate to omeprazole in patients with nonerosive reflux disease: a randomized clinical trial," Dis. Esophag. 25(5):373-380, Oxford Academic Press, United Kingdom (2011).

Olivera, A.C. et al., "Potassium urinary excretion and dietary intake: a cross-sectional anaylsis in 8-10 year old children," BMC Pediatrics 15:60, BioMed Central, United (2015) (10 pages).

Ranvirsingh, T.A. et al., "Formulation and Evaluation of Floating Alginate Beads on Anti Ulcer Drug" Int. J. Pharm. Sci. Rev. Res. 21(2):120-124, Global Research Online, India (2013).

Saied, N., et al., "Assesment of Sodium and Potassium Intakes in Children Aged 6 to 18 Years by 24th Urinary Excretion in City of Rabat, Morocco," J. Nutr. Metab. 2018:8687192, Hindawi Publishing, United Arab Emirates (2018).

Tian, N., et al., "Sodium and potassium intakes among US infants and preschool children, 2003-2010," Am. J. Clinc. Nutr. 98:1113-1122, American Society Nutrition, United States (2013).

Highlights of Prescribing Information for "KONVOMEP™ (omeprazole and sodium biocarbonate for oral suspension)", intitial U.S. Approval 2004, the U.S. Food and Drug Administration, United States, revised Aug. 2022.

* cited by examiner

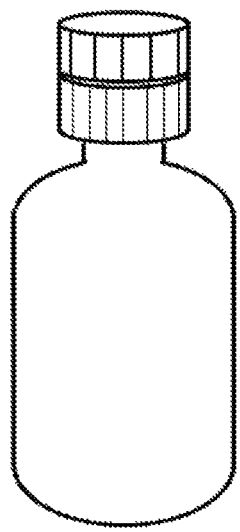
PICS Cap containing drug loaded powder:
- Omeprazole
- Sodium hydrogen carbonate
- Sodium alginate
- Mannitol
Bottle containing diluent powder:
- Sodium hydrogen carbonate
- Potassium hydrogen carbonate
- Sodium alginate
- Mannitol
- Sucralose
- Xanthan gum
- Sodium benzoate
- Methyl paraben sodium
- Maltitol
- Titanium dioxide
- Flavouring(s)

PEDIATRIC SUSPENSION FORMULATION

BACKGROUND

Omeprazole, 5-methoxy-2-[(4-methoxy-3,5-dimethyl-2-pyridinyl)methyl]sulfinyl-1H-benzimidazole, inhibits gastric acid secretion. Omeprazole belongs to a class of antisecretory compounds, the substituted benzimidazoles, that do not exhibit anticholinergic or $H_2$ histamine antagonist properties. Drugs of this class of compounds suppress gastric acid secretion by the specific inhibition of the $H^+/K^+$ ATPase enzyme system at the secretory surface of the gastric cell and are called proton pump inhibitors.

Proton pump inhibitors, such as omeprazole, are acid labile and thus they are rapidly degraded in acidic media, such as the contents of the stomach, but they have an acceptable stability under alkaline conditions. Absorption of orally administered proton pump inhibitors, such as omeprazole, take place in the small intestine.

In order to solve the stability problems of omeprazole in acidic conditions, some omeprazole dosage forms available on the market incorporate omeprazole as enteric coated granules or pellets in delayed release solid oral dosage forms. Examples of such dosage forms include, for example, Losec® and Losec MUPS® which both contain enteric coated pellets of omeprazole in hard gastro-resistant capsules and gastro-resistant tablets, respectively.

Commonly, pediatric subjects encounter difficulty being administered solid oral dosage forms, such as tablets or capsules.

Currently, no oral liquid dosage form of omeprazole is approved in Europe. In the United States, omeprazole powder for oral suspension is sold under the trade name Zegerid® which is a white, flavored powder packaged in single-dose packets which are constituted with water prior to administration. Each packet contains either 20 mg or 40 mg of omeprazole and 1680 mg of sodium bicarbonate, and the following excipients: xylitol, sucrose, sucralose, xanthan gum, and flavorings. One dose of Zegerid® Powder for Oral Suspension contains 460 mg of sodium $Na^-$). (Also available in the United States is a FIRST®-Omeprazole Compounding Kit that is comprised of omeprazole powder and FIRST-PPI (proton pump inhibitor) Suspension containing artificial strawberry flavor, benzyl alcohol, FD&C Red No. 40, Magnasweet 100 (ammonium glycyrrhizate), poloxamer 188, propylene glycol, purified water, simethicone emulsion, sodium bicarbonate, sodium citrate (dihydrate), sucralose, and xanthan gum. When compounded, the final product provides a homogenous suspension containing 2 mg/ml of omeprazole in FIRST®-PPI Suspension. These omeprazole suspension formulations contain high amounts of sodium which makes these formulations unacceptable for pediatric subjects.

There is a need for a liquid oral omeprazole formulation designed especially for pediatric subjects.

BRIEF SUMMARY

The present disclosure relates to storage-stable proton pump inhibitor (PPI) systems comprising a therapeutically effective amount of a PPI or a pharmaceutically acceptable salt thereof, such as omeprazole or a pharmaceutically acceptable salt thereof, which upon constitution with water contain sodium at acceptable levels for use in therapy in pediatric subjects. The storage stable PPI systems are specifically suitable for use in multi-dose dosage forms. The present disclosure also relates to oral pharmaceutical suspensions comprising water and a pharmaceutically effective amount of a PPI or a pharmaceutically acceptable salt thereof, such as omeprazole or a pharmaceutically acceptable salt thereof, and one or more buffering agents. The oral pharmaceutical suspension of the present disclosure has an acceptable level of buffering capacity for pediatric subjects. In some aspects, the buffering capacity of the oral pharmaceutical suspensions described herein is about 2 mEq/ml of the oral suspension.

In one aspect, the present disclosure provides a storage-stable omeprazole system, the system comprising a therapeutically effective amount of omeprazole, or a pharmaceutically acceptable salt thereof, wherein the system contains a percentage of moisture of no more than about 2.5%, and wherein the system contains no sodium from a sodium-containing buffering agent or contains sodium and potassium at a ratio of from about 1:2.6 to about 1:3.4 by weight, and further wherein the storage-stable omeprazole system is constituted with water prior to administration. In some embodiments of this aspect, the sodium and potassium are present at a ratio of about 1:3.2 by weight. In some embodiments, the system has a moisture content of about 0.5% to about 1.5%.

In some embodiments, the storage-stable omeprazole system further comprises a pharmaceutically acceptable desiccant. In some embodiments, the pharmaceutically acceptable desiccant is sodium alginate.

In another aspect, the present disclosure provides a storage-stable omeprazole system, the system comprising (i) a first mixture comprising (a) a therapeutically effective amount of omeprazole, or a pharmaceutically acceptable salt thereof, wherein the first mixture contains a percentage of moisture of no more than about 2.5%; and (ii) a second mixture comprising a second buffering agent, wherein the second mixture contains a percentage of moisture of no more than about 2.5%; wherein the first mixture and the second mixture are stored separately from each other and are mixed together on or just before constitution with water, and wherein the system contains no sodium from a sodium-containing buffering agent or contains sodium and potassium at a ratio of from about 1:2.6 to about 1:3.4 by weight. In some embodiments, the sodium and potassium are present at a ratio of about 1:3.2 by weight. In some embodiments, the first mixture further comprises (b) a first desiccant. In some embodiments, the first mixture further comprises (c) a first buffering agent. In some embodiments, the first mixture further comprises both (b) the first desiccant and (c) the first buffering agent. In some embodiments, the second mixture further comprises a second desiccant.

In another aspect, the present disclosure provides a storage-stable omeprazole system formulated in a drug delivery device suitable for multi-dose administration of omeprazole, or the pharmaceutically acceptable salt thereof, the system comprising a therapeutically effective amount of omeprazole, or a pharmaceutically acceptable salt thereof, wherein the system contains a percentage of moisture of no more than about 2.5%, and wherein the system contains no sodium from a sodium-containing buffering agent or the system contains sodium and potassium at a ratio of from about 1:2.6 to about 1:3.4 by weight, and further wherein the storage-stable omeprazole system is constituted with water prior to administration.

In another aspect, the present disclosure provides a storage-stable omeprazole powder system, the system comprising (i) a first powder mixture comprising (a) a therapeutically effective amount of omeprazole, or a pharmaceutically acceptable salt thereof, (b) sodium alginate, and (c) a first buffering agent; and (ii) a second powder mixture comprising sodium alginate and a second buffering agent, wherein the first powder mixture and the second powder mixture are stored separately from each other and are mixed together on or just before constitution with water, wherein the system contains sodium and potassium at a ratio of from about 1:2.6 to about 1:3.4 by weight. In some embodiments, the sodium and potassium are present at a ratio of about 1:3.2 by weight.

In another aspect, the present disclosure provides an oral pharmaceutical suspension, comprising water, a pharmaceutically effective amount of omeprazole, or a pharmaceutically acceptable salt thereof, dispersed in the water, and one or more buffering agents, and wherein the suspension contains no sodium from a sodium-containing buffering agent or the suspension contains sodium and potassium at a ratio of from about 1:2.6 to about 1:3.4 by weight.

In some embodiments, the oral pharmaceutical suspension, comprises water, a pharmaceutically effective amount of omeprazole, or a pharmaceutically acceptable salt thereof, dispersed in the water, and one of more buffering agents, wherein the suspension contains sodium and potassium at a ratio of from about 1:2.6 to about 1:3.4 by weight.

In some embodiments, the omeprazole, or a pharmaceutically acceptable salt thereof, in the storage-stable omeprazole systems or oral pharmaceutical suspensions described herein is micronized. In some embodiments, the storage-stable omeprazole systems or oral pharmaceutical suspensions described herein contain a mixture of micronized and non-micronized omeprazole or a pharmaceutically acceptable salt thereof. In some embodiments, the storage-stable omeprazole system, or specifically the storage-stable omeprazole powder system, is provided in a drug delivery device suitable for multi-dose administration of omeprazole or a pharmaceutically acceptable salt thereof.

In some embodiments, the storage-stable omeprazole system described herein remains stable at 25° C./60% relative humidity for at least 2 years.

In some embodiments, the oral pharmaceutical suspension of the present disclosure provides a biphasic pharmacokinetic profile having a first and second $C_{max}$ and a first and second $T_{max}$ following oral administration in a subject in need thereof.

In another aspect, the present disclosure provides a method of inhibiting gastric acid secretion in a subject in need thereof. In certain embodiments, the method comprises administering to a subject in need thereof an effective amount of an oral pharmaceutical suspension comprising water, a pharmaceutically effective amount of omeprazole, or a pharmaceutically acceptable salt thereof, dispersed in the water, and one or more buffering agents, wherein the suspension contains no sodium from a sodium-containing buffering agent or the suspension contains sodium and potassium at a ratio of from about 1:2.6 to about 1:3.4 by weight. In some embodiments, the method comprises administering to a subject in need thereof an effective amount of an oral pharmaceutical suspension comprising water, a pharmaceutically effective amount of omeprazole, or a pharmaceutically acceptable salt thereof, dispersed in the water, and one or more buffering agents, wherein the suspension contains sodium and potassium at a ratio of from about 1:2.6 to about 1:3.4 by weight. In some embodiments, the subject is a child. In some embodiments, the suspension comprises from about 1 mg/ml to about 10 mg/ml of omeprazole or a pharmaceutically acceptable salt thereof.

In another aspect, the present disclosure provides a method of preparing an oral pharmaceutical suspension. Typically, the method comprises combining a first mixture comprising (a) a therapeutically effective amount of omeprazole, or a pharmaceutically acceptable salt thereof, wherein the first mixture contains a percentage of moisture of no more than about 2.5%; with a second mixture comprising a second buffering agent; wherein the second mixture contains a percentage of moisture of no more than about 2.5%; to obtain a combined mixture, wherein the combined mixture contains no sodium from a sodium-containing buffering agent or the combined mixture contains sodium and potassium at a ratio of from about 1:2.6 to about 1:3.4 by weight; and adding water to the combined mixture. In some embodiments, the second mixture further comprises a second desiccant. In some embodiments, the method comprises combining a first mixture comprising (a) a therapeutically effective amount of omeprazole, or a pharmaceutically acceptable salt thereof, containing a percentage of moisture of no more than about 2.5%; with a second mixture comprising a second desiccant and a second buffering agent; to obtain a combined mixture, wherein the combined mixture contains sodium and potassium at a ratio of from about 1:2.6 to about 1:3.4; and adding water to the combined mixture. In some embodiments, the first mixture further comprises (b) a first desiccant. In some embodiments, the first mixture further comprises (c) a first buffering agent. In some embodiments, the first mixture further comprises both (b) the first desiccant and (c) the first buffering agent.

In another aspect, the present disclosure provides a method of inhibiting gastric acid secretion, comprising administering to a subject in need thereof an effective amount of an oral pharmaceutical suspension comprising water, a pharmaceutically effective amount of omeprazole, or a pharmaceutically acceptable salt thereof, dispersed in the water, and one or more buffering agents, wherein the suspension contains no sodium from a sodium-containing buffering agent or the suspension contains sodium and potassium at a ratio of from about 1:2.6 to about 1:3.4 by weight; and wherein the oral pharmaceutical suspension is prepared by combining a first mixture comprising (a) a therapeutically effective amount of omeprazole, or a pharmaceutically acceptable salt thereof, wherein the first mixture contains a percentage of moisture of no more than about 2.5%; with a second mixture comprising a second buffering agent, wherein the second mixture contains a percentage of moisture of no more than about 2.5%; to obtain a combined mixture, wherein the combined mixture contains no sodium from a sodium-containing buffering agent or the combined mixture contains sodium and potassium at a ratio of from about 1:2.6 to about 1:3.4 by weight; and adding water to the combined mixture. In some embodiments, the second mixture further comprises a second desiccant. In some embodiments, the method comprises administering to a subject in need thereof an effective amount of an oral pharmaceutical suspension comprising water, a pharmaceutically effective amount of omeprazole, or a pharmaceutically acceptable salt thereof, dispersed in the water, and one or more buffering agents, wherein the suspension contains sodium and potassium at a ratio of from about 1:2.6 to about 1:3.4 by weight, wherein the oral pharmaceutical suspension is prepared by combining a first mixture comprising (a) a therapeutically effective amount of omeprazole, or a pharmaceutically acceptable salt thereof, wherein the first mixture contains a percentage of moisture of no more than about 2.5%; with a second mixture comprising a second desiccant and a second buffering agent; to obtain a combined mixture, wherein the combined mixture contains sodium and potassium at a ratio of from about 1:2.6 to about 1:3.4; and adding water to the combined mixture. In some embodiments, the first mixture further comprises (c) a first buffering agent. In some embodiments, the first mixture further comprises both (b) the first desiccant and (c) the first buffering agent.

Additional embodiments and advantages described herein will be set forth, in part, in the description that follows, and will flow from the description, or can be learned by practice described herein. The embodiments and advantages described herein will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF DRAWINGS

FIG. 1 depicts a delivery device suitable for use for storage-stable systems of the present disclosure.

DETAILED DESCRIPTION

The headings provided herein are not limitations of the various aspects described herein, which can be defined by reference to the specification as a whole. It is also to be understood that the terminology used herein is for the purpose of describing particular aspects only, and is not intended to be limiting, since the scope of the present disclosure will be limited only by the appended claims.

Definitions

For convenience, the meaning of some terms and phrases used in the specification, examples, and appended claims are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

The articles "a," "an," and "the" are used herein to refer to one or to more than one (i.e., to at least one) of the grammatical object of the article. By way of example, "an element" means one element or more than one element.

As used herein, the term "about" means±10% of the specified value, unless otherwise indicated.

The term "at least" prior to a number or series of numbers is understood to include the number adjacent to the term "at least," and all subsequent numbers or integers that could logically be included, as clear from context. When at least is present before a series of numbers or a range, it is understood that "at least" can modify each of the numbers in the series or range.

The term "no more than" prior to a number or series of numbers is understood to include the number adjacent to the term "no more than," and all preceding numbers or integers that could logically be included, as clear from context. When "no more than" is present before a series of numbers or a range, it is understood that "no more than" can modify each of the numbers in the series or range.

As used herein, the terms "comprises," "comprising," "having," "including," "containing," and the like are open-ended terms meaning "including, but not limited to." To the extent a given embodiment disclosed herein "comprises" certain elements, it should be understood that present disclosure also specifically contemplates and discloses embodiments that "consist essentially of" those elements and that "consist of" those elements.

The terms "treat," "treating," and "treatment" refer to any indicia of success in the treatment or amelioration of an injury, disease, or condition, including any objective or subjective parameter such as abatement; remission; diminishing of symptoms or making the injury, disease, or condition more tolerable to the patient; slowing in the rate of degeneration or decline; or improving a patient's physical or mental well-being. The treatment or amelioration of symptoms can be based on objective or subject parameters, including the results of a physical examination, neuropsychiatric examinations, or psychiatric evaluation.

By an "effective" amount or a "therapeutically effective amount" or "a pharmaceutically effective amount" of a drug or pharmacologically active agent is meant a nontoxic but sufficient amount of the drug or agent to provide the desired effect. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The term "pharmaceutically acceptable salt" refers to salts prepared from pharmaceutically acceptable inorganic and organic acids.

The terms "desiccant," "first desiccant," and "second desiccant" as used herein refer to a pharmaceutically acceptable hygroscopic material that serves to maintain a state of dryness. These desiccants serve to eliminate humidity from the air and they adsorb moisture, thereby creating and sustaining a dry, moisture-free environment. Suitable pharmaceutically acceptable desiccants include, for example, sodium alginate, starch, and the like.

The term "buffering agent" or "buffer" mean any pharmaceutically acceptable weak base or strong base and mixtures thereof which, when formulated or delivered before, during and/or after the proton pump inhibitor, such as omeprazole, functions to substantially prevent or inhibit acid degradation of the proton pump inhibitor by gastric acid and to preserve the oral bioavailability of the proton pump inhibitor.

The term "percentage of moisture" refers to a value measured using Loss on Drying (LOD) method which involves heating a sample (e.g., sodium alginate or omeprazole) at 90° C. for 5 minutes and determining the % weight loss.

The term "multi-dose", as used herein, means that the omeprazole powder system, after being constituted with water, can be administered in multiple doses over a period of time, e.g., for more than 7 days, more than 14 days, or more than 28 days.

The term "stable" or "storage-stable," as used herein, refers to chemical stability, wherein not more than 5% w/w of total related substances, e.g. omeprazole degradation products, are formed on storage at 40° C. and 75% relative humidity (RH) for a period of at least 6 months, or at 25° C. and 60% relative humidity for at least 2 years, to the extent necessary for the sale and use of the omeprazole powder system described herein.

As used herein, the phrase "low viscosity grade sodium alginate" refers to sodium alginates having solution viscosities of less than about 100 millipascal second (mPa·s) in 3% aqueous solutions. Suitable low viscosity grade sodium alginates include, for example, Manucol® LB (by FMC Biopolymer).

The term "GERD" refers to gastro-esophageal reflux disease. This is a disease where acid from the stomach escapes into the gullet (the tube which connects the throat to the stomach) causing pain, inflammation, and heartburn. In children, the symptoms of the condition can include the return of stomach contents into the mouth (regurgitation), being sick (vomiting), and poor weight gain.

The term "PICS" refers to Protection In Situ Constitution System. The PICS system is a bottle with an integrated cap as shown in FIG. 1. Omeprazole (or any PPI) containing mixture is in a dry form in the cap until the point of constitution. A diluent phase, such as the second mixture described below, is included in the bottle. At the time of constitution, the drug loaded mixture is released from the cap into the diluent phase (or the second mixture) by twisting the cap and subsequently water is added for constitution.

As used herein, the term "child" is a human being between the stages of birth and puberty.

The term "puberty" is the process of physical changes through which a child's body matures into an adult body capable of sexual reproduction. On average, girls begin puberty around ages 10-11 and end puberty around 15-17; boys begin around ages 11-12 and end around 16-17.

As used herein, the term "infant" is the synonym for "baby," the very young offspring of a human. The term "infant" is typically applied to young children under one year of age.

As used herein, the term "toddler" refers to a child of 12 to 36 months old.

As used herein, the term "preadolescent" refers to a person of 10-13 years old.

As used herein, the term "adolescent" refers to a person between ages 10 and 19.

Storage-Stable Systems Described Herein

Although proton pump inhibitors, such as omeprazole, are widely used for treatment of gastric acid-mediated disorders in patients, their chemical instability in acidic media does not allow formulation of simple aqueous dosage forms for therapy. The present disclosure provides storage-stable PPI systems that upon constitution with water provide oral pharmaceutical PPI suspensions for administering effective amounts of a PPI or a pharmaceutically acceptable salt thereof, such as omeprazole or a pharmaceutically acceptable salt thereof, to a subject in need thereof, while having acceptable levels of sodium for administering to pediatric subjects. The oral pharmaceutical suspensions of the present disclosure have an acceptable buffering capacity for pediatric subjects. In some embodiments, the buffering capacity of the oral pharmaceutical suspensions described herein is about 2 mEq/ml of the oral suspension. This is achieved, for example, by using a balanced buffering system based on sodium bicarbonate and potassium bicarbonate. In some embodiments, the buffering capacity of the oral pharmaceutical suspensions described herein is from about 0.5 mEq/ml to about 4 mEq/ml of the oral suspension. In some embodiments, the buffering capacity of the oral pharmaceutical suspensions described herein is from about 1.6 mEq/ml to about 2.3 mEq/ml of the oral suspension.

In one aspect, the present disclosure provides a storage-stable PPI system (such as a storage-stable omeprazole system), the system comprising a therapeutically effective amount of a PPI or a pharmaceutically acceptable salt thereof, such as omeprazole, or a pharmaceutically acceptable salt thereof, wherein the system contains a percentage of moisture of no more than about 2.5%, and wherein the system contains no sodium from a sodium-containing buffering agent or contains sodium and potassium at a ratio of from about 1:100 to about 100:1 by weight, and further wherein the storage-stable PPI system is constituted with water prior to administration. In certain embodiments, the storage-stable PPI system contains sodium and potassium at a ratio of from about 1:50 to about 50:1 by weight. In certain embodiments, the storage-stable PPI system contains sodium and potassium at a ratio of from about 1:10 to about 10:1 by weight. In certain embodiments, the storage-stable PPI system contains sodium and potassium at a ratio of from about 1:2 to about 1:5 by weight.

In some embodiments, the storage-stable PPI system (such as a storage-stable omeprazole system) contains no sodium from a sodium-containing buffering agent such as sodium carbonate, sodium bicarbonate, sodium dihydrogen phosphate, sodium hydrogen phosphate, trisodium phosphate, sodium dihydrogen citrate, disodium hydrogen citrate, trisodium citrate, sodium tetraborate, sodium acetate, disodium hydrogen phthalate, sodium hydrogen phthalate, sodium bitartrate, disodium tartrate, and sodium succinate.

In some embodiments, the storage-stable PPI system (such as a storage-stable omeprazole system) comprises a therapeutically effective amount of a PPI or a pharmaceutically acceptable salt thereof, such as omeprazole or a pharmaceutically acceptable salt thereof, wherein the system contains a percentage of moisture of no more than about 2.5%, and wherein the system contains sodium and potassium at a ratio of from about 1:2.6 to about 1:3.4 by weight, and further wherein the storage-stable PPI system is constituted with water prior to administration. In some embodiments of this aspect, the sodium and potassium are present at a ratio of about 1:3.2 by weight.

In some embodiments, the storage-stable PPI system (such as a storage-stable omeprazole system) has a moisture content of about 0.5% to about 1.5%. In some embodiments, the storage-stable PPI system (such as a storage-stable omeprazole system) has a percentage of moisture of no more than about 1%.

Suitable PPIs (proton pump inhibitors) that can be used in the storage-stable PPI system described herein include, for example, omeprazole, hydroxyomeprazole, esomeprazole, lansoprazole, pantoprazole, dexlansoprazole, rapeprazole, dontoprazole, tenatoprazole, haberprazole, ransoprazole, pariprazole, and leminoprazole, and the pharmaceutically acceptable salts thereof. In some embodiments, the PPI is selected from the group consisting of omeprazole, esomeprazole, lansoprazole, pantoprazole, dexlandoprazole, rabeprazole, and the pharmaceutically acceptable salts thereof. In some embodiments, the PPI is omeprazole or esomeprazole, or a pharmaceutically acceptable salt thereof. Examples of suitable PPI pharmaceutically acceptable salts include, for example, sodium, magnesium, calcium and potassium salts, such as for example, omeprazole sodium salt, omeprazole magnesium salt, omeprazole calcium salt, omeprazole potassium salt, esomeprazole sodium salt, esomeprazole magnesium salt, esomeprazole calcium salt, and esomeprazole potassium salt.

In some embodiments, the PPI is omeprazole or a pharmaceutically acceptable salt thereof. In some embodiments, the PPI is omeprazole (i.e., the neutral form of omeprazole without a salt forming cation present). In some embodiments, the PPI is esomeprazole or a pharmaceutically acceptable salt thereof. In some embodiments, the PPI is esomeprazole (i.e., the neutral form of esomeprazole without a salt forming cation present).

In some embodiments, the storage-stable PPI system further comprises a desiccant. Suitable desiccants include any desiccants that are pharmaceutically acceptable and serve to maintain dryness by eliminating humidity from the air and absorbing moisture, thereby creating and sustaining a dry, moisture-free environment for the PPI. Suitable pharmaceutically acceptable desiccants include, for example, sodium alginate, starch, and the like. In some embodiments, the desiccant is sodium alginate. The desiccant can comprise one pharmaceutically acceptable desiccant or a mixture of two or more pharmaceutically acceptable desiccants.

In some embodiments, the sodium alginate present in the storage-stable PPI systems described herein is dry, i.e., the sodium alginate contains a percentage of moisture of less than about 2%. In some embodiments, the storage-stable PPI systems comprise dry sodium alginate that has a moisture content of about 0.5% to about 1.5%.

In some embodiments, the sodium alginate present in storage-stable PPI systems described herein, such as in storage-stable omeprazole systems, is low viscosity grade sodium alginate. Suitable low viscosity grade sodium alginates have solution viscosities of less than about 100 millipascal second (mPa·s) in 3% aqueous solutions. Examples of suitable low viscosity grade sodium alginates include Manucol® LB (by FMC Biopolymer).

In some embodiments, storage-stable PPI systems described herein, such as storage-stable omeprazole systems, comprise one or more buffering agents. In some embodiments, storage-stable PPI systems described herein comprise 1, 2, 3, or 4 buffering agents. In some embodiments, storage-stable PPI systems described herein comprise one buffering agent. In some embodiments, storage-stable PPI systems described herein comprise 2 or 3 buffering agents. In some embodiments, storage-stable PPI systems described herein comprise 2 buffering agents.

The storage-stable PPI system described herein, such as the storage-stable omeprazole system, can comprise any suitable buffering agent that functions to substantially prevent or inhibit the acid degradation of the PPI (such as omeprazole or a pharmaceutically acceptable salt thereof) by gastric acid sufficient to preserve the bioavailability of the PPI administered. In some embodiments, the one or more buffering agents are each independently selected from the group consisting of alkali metal or alkaline earth metal carbonates, bicarbonates, phosphates, citrates, borates, acetates, phthalates, tartrates, and succinates. In some embodiments, the one or more buffering agents are each independently selected from sodium or potassium carbonates, bicarbonates, phosphates, citrates, borates, acetates, phthalates, tartrates, and succinates.

In some embodiments, storage-stable PPI systems described herein (such as storage-stable omeprazole systems) comprise at least one buffering agent selected from sodium carbonate, sodium bicarbonate, sodium dihydrogen phosphate, sodium hydrogen phosphate, trisodium phosphate, sodium dihydrogen citrate, disodium hydrogen citrate, trisodium citrate, sodium tetraborate, sodium acetate, disodium hydrogen phthalate, sodium hydrogen phthalate, sodium bitartrate, disodium tartrate, and sodium succinate. In some embodiments, storage-stable PPI systems described herein (such as storage-stable omeprazole systems) comprise at least one buffering agent selected from potassium carbonate, potassium bicarbonate, potassium dihydrogen phosphate, potassium hydrogen phosphate, tripotassium phosphate, potassium dihydrogen citrate, dipotassium hydrogen citrate, tripotassium citrate, potassium tetraborate, potassium acetate, dipotassium hydrogen phthalate, potassium hydrogen phthalate, potassium bitartrate, dipotassium tartrate, and potassium succinate.

In some embodiments, storage-stable PPI systems described herein (such as storage-stable omeprazole systems) comprise no more than one buffering agent selected from potassium carbonate, potassium bicarbonate, potassium dihydrogen phosphate, potassium hydrogen phosphate, tripotassium phosphate, potassium dihydrogen citrate, dipotassium hydrogen citrate, tripotassium citrate, potassium tetraborate, potassium acetate, dipotassium hydrogen phthalate, potassium hydrogen phthalate, potassium bitartrate, dipotassium tartrate, and potassium succinate. In some embodiments, the one buffering agent is potassium bicarbonate.

In some embodiments, storage-stable PPI systems described herein (such as storage-stable omeprazole systems) comprise two or more buffering agents selected from sodium and potassium carbonates, bicarbonates, phosphates, citrates, borates, acetates, phthalates, tartrates, and succinates. In some embodiments, storage-stable PPI systems described herein comprise both sodium bicarbonate and potassium bicarbonate. In some embodiments, sodium bicarbonate and potassium bicarbonate are present in the system at a ratio of about 1:100 to about 100:1 by weight. In some embodiments, sodium bicarbonate and potassium bicarbonate are present in the system at a ratio of about 1:50 to about 50:1 by weight. In some embodiments, sodium bicarbonate and potassium bicarbonate are present in the system at a ratio of about 1:10 to about 10:1 by weight. In some embodiments, sodium bicarbonate and potassium bicarbonate are present in the system at a ratio of about 1:2 to about 1:5 by weight. In some embodiments, sodium bicarbonate and potassium bicarbonate are present in the system at a ratio of about 1:2.5 to about 1:3.4 by weight. In some embodiments, sodium bicarbonate and potassium bicarbonate are present at a ratio of about 1:2.7 by weight.

The one or more buffering agents present in the storage-stable PPI systems described herein (such as storage-stable omeprazole systems) in an amount sufficient to increase gastric fluid pH to a pH that prevents degradation of at least some of the PPI (such as omeprazole or a pharmaceutically acceptable salt thereof) in the gastric fluid.

In some embodiments, the one or more buffering agents provide a buffering capacity of from about 0.5 to about 4 mEq/ml dose of constituted storage-stable PPI system described herein with water. In some embodiments, the one or more buffering agents provide a buffering capacity of from about 1.6 to about 2.3 mEq/ml dose of constituted storage-stable PPI system described herein with water. In some embodiments, the one or more buffering agents provide a buffering capacity of about 2 mEq/ml dose of constituted storage-stable PPI system described herein with water.

In some embodiments, the one or more buffering agents provide a buffering capacity of from about 0.5 to about 4 mEq/ml dose of constituted storage-stable omeprazole system described herein with water. In some embodiments, the one or more buffering agents provide a buffering capacity of from about 1.6 to about 2.3 mEq/ml dose of constituted storage-stable omeprazole system described herein with water. In some embodiments, the one or more buffering agents provide a buffering capacity of about 2 mEq/ml dose of constituted storage-stable omeprazole system described herein with water.

Storage-stable PPI systems described herein (such as storage-stable omeprazole systems) can be prepared in any suitable multi-particulate dosage form that provides an oral suspension when dispersed in water. Suitable dosage forms include, but are not limited to, a powder, a pellet, a granule, a seed, a bead, a spheroid, a microsphere, or mixtures thereof. In some embodiments, storage-stable PPI systems described herein (such as storage-stable omeprazole systems) are in the form of a powder or a pellet. Suitable powders, pellets, granules, seeds, beads, spheroids, microspheres, and mixtures thereof, can be prepared by conventional pharmacological techniques known in the art.

In some aspects, storage-stable PPI systems described herein (such as storage-stable omeprazole systems) comprise (i) a first mixture comprising (a) a therapeutically effective amount of a PPI or a pharmaceutically acceptable salt there (such as omeprazole, or a pharmaceutically acceptable salt thereof), wherein the first mixture contains a percentage of moisture of no more than about 2.5%; and (ii) a second mixture comprising a second buffering agent, wherein the second mixture contains a percentage of moisture of no more than about 2.5%; wherein the first mixture and the second mixture are stored separately from each other and are mixed together on or just before constitution with water, and wherein the system contains no sodium from a sodium-containing buffering agent or contains sodium and potassium at a ratio of from about 1:100 to about 100:1 by weight. In certain embodiments, the storage-stable PPI system contains sodium and potassium at a ratio of from about 1:50 to about 50:1 by weight. In certain embodiments, the storage-stable PPI system contains sodium and potassium at a ratio of from about 1:10 to about 10:1 by weight. In certain embodiments, the storage-stable PPI system contains sodium and potassium at a ratio of from about 1:2 to about 1:5 by weight.

In some embodiments, storage-stable PPI systems described herein (such as storage-stable omeprazole systems) comprise (i) a first mixture comprising (a) a therapeutically effective amount of a PPI or a pharmaceutically acceptable salt there (such as omeprazole, or a pharmaceutically acceptable salt thereof), wherein the first mixture contains a percentage of moisture of no more than about 2.5%; and (ii) a second mixture comprising a second buffering agent, wherein the second mixture contains a percentage of moisture of no more than about 2.5%; wherein the first mixture and the second mixture are stored separately from each other and are mixed together on or just before constitution with water, and wherein the system contains no sodium from a sodium-containing buffering agent or contains sodium and potassium at a ratio of from about 1:2.6 to about 1:3.4 by weight. In some embodiments, the sodium and potassium are present at a ratio of about 1:3.2 by weight.

In some embodiments, the storage-stable PPI system (such as a storage-stable omeprazole system) contains no sodium from a sodium-containing buffering agent.

In some embodiments, the first mixture further comprises (b) a first desiccant and/or the second mixture further comprises a second desiccant.

In some embodiments, storage-stable PPI systems described herein (such as storage-stable omeprazole systems) comprise (i) a first mixture comprising (a) a therapeutically effective amount of a PPI or a pharmaceutically acceptable salt thereof (such as omeprazole or a pharmaceutically acceptable salt thereof), wherein the first mixture contains a percentage of moisture of no more than about 2.5%; and (ii) a second mixture comprising a second desiccant and a second buffering agent, wherein the first mixture and the second mixture are stored separately from each other and are mixed together on or just before constitution with water, and wherein the system contains sodium and potassium at a ratio of from about 1:2.6 to about 1:3.4 by weight. In some embodiments of this aspect, storage-stable PPI systems described herein (such as storage-stable omeprazole systems) contain sodium and potassium at a ratio of about 1:3.2 by weight.

In some embodiments, the first mixture and the second mixture each independently have a moisture content of about 0.5% to about 1.5%. In some embodiments, the first mixture and the second mixture have each independently a moisture content of about 0.6% to about 1.1%. In some embodiments, the first mixture and the second mixture have each independently a moisture content of about 0.5% to about 0.9%. In some embodiments, the first mixture has a moisture content of about 0.5% to about 1.5% and the second mixture has a moisture content of no more than about 1.5%. In some embodiments, the second mixture has a moisture content of no more than about 0.5%.

In some embodiments, the first mixture further comprises (b) a first desiccant.

In some embodiments, the first mixture further comprises (c) a first buffering agent.

In some embodiments, storage-stable PPI systems described herein (such storage-stable omeprazole systems) comprise (i) a first mixture comprising (a) a therapeutically effective amount of a PPI or a pharmaceutically acceptable salt thereof (such as omeprazole or a pharmaceutically acceptable salt thereof), (b) a first desiccant, and (c) a first buffering agent, wherein the first mixture contains a percentage of moisture of no more than about 2.5%; and (ii) a second mixture comprising a second desiccant and a second buffering agent, wherein the first mixture and the second mixture are stored separately from each other and are mixed together on or just before constitution with water, and wherein the system contains sodium and potassium at a ratio of from about 1:2.6 to about 1:3.4 by weight. In some embodiments of this aspect, storage-stable PPI systems described herein (such as storage-stable omeprazole systems) contain sodium and potassium at a ratio of about 1:3.2 by weight. In some embodiments, the first mixture and the second mixture each independently have a moisture content of about 0.5% to about 1.5%. In some embodiments, the first mixture and the second mixture have each independently a moisture content of about 0.6% to about 1.1%. In some embodiments, the first mixture and the second mixture have each independently a moisture content of about 0.5% to about 0.9%. In some embodiments, the first mixture has a moisture content of about 0.5% to about 1.5% and the second mixture has a moisture content of no more than about 1.5%. In some embodiments, the second mixture has a moisture content of no more than about 0.5%.

The first desiccant and the second desiccant can comprise any pharmaceutically acceptable desiccant as defined above or a mixture of two or more pharmaceutically acceptable desiccants. The first desiccant and the second desiccant can be the same or different. In some embodiments, the first desiccant is the same as the second desiccant. In some embodiments, the first desiccant and the second desiccant are different. In some embodiments, the first desiccant and the second desiccant are sodium alginate. In some embodiments, the sodium alginate is dry, i.e., the sodium alginate contains a percentage of moisture of less than about 2%. In some embodiments, the dry sodium alginate has a moisture content of about 0.5% to about 1.5%.

In some embodiments, the first mixture and the second mixture can be, independently, in the form of a powder, a pellet, a granule, a seed, a bead, a spheroid, a microsphere, or mixtures thereof. In some embodiments, the first mixture and the second mixture are each independently in the form of a powder or a pellet. In other embodiments, the first mixture and the second mixture can both be in the form of a powder.

In some embodiments, the PPI or a pharmaceutically acceptable salt thereof, such as omeprazole or a pharmaceutically acceptable salt thereof, present in the storage-stable systems described herein is micronized.

In some embodiments, the PPI or a pharmaceutically acceptable salt thereof is present in the storage-stable systems described herein, is a mixture of micronized and non-micronized PPI or a pharmaceutically acceptable salt thereof. In some embodiments of this aspect, the PPI or a pharmaceutically acceptable salt thereof comprises from about 30% to about 70% by weight micronized PPI or the pharmaceutically acceptable salt and the rest is non-micronized. In some embodiments, the PPI or a pharmaceutically acceptable salt thereof is a 1:1 mixture, by weight, of micronized and non-micronized PPI or the pharmaceutically acceptable salt thereof. In some embodiments, the PPI or a pharmaceutically acceptable salt thereof is about a 1:2, 1:3, 1:4, 1:5, 1:6, 1:7, 1:8, or 1:9 mixture, by weight of micronized and non-micronized PPI or the pharmaceutically acceptable salt thereof. In some embodiments, the PPI or a pharmaceutically acceptable salt thereof is about a 1:2.3 mixture (i.e., about a 30:70 mixture) by weight of micronized and non-micronized PPI or the pharmaceutically acceptable salt thereof. In some embodiments, the PPI or a pharmaceutically acceptable salt thereof is about a 1:2, 1:3, 1:4, 1:5, 1:6, 1:7, 1:8, or 1:9 mixture, by weight of non-micronized and micronized PPI or the pharmaceutically acceptable salt thereof. In some embodiments, the PPI or a pharmaceutically acceptable salt thereof is about a 1:1.5 mixture (i.e., about a 40:60 mixture) by weight of non-micronized and micronized PPI or the pharmaceutically acceptable salt thereof.

In some embodiments, the omeprazole or a pharmaceutically acceptable salt thereof present in the storage-stable omeprazole systems described herein is a mixture of micronized and non-micronized omeprazole or a pharmaceutically acceptable salt thereof. In some embodiments, the omeprazole or a pharmaceutically acceptable salt thereof comprises from about 30% to about 70% by weight micronized omeprazole or the pharmaceutically acceptable salt and the rest is non-micronized. In some embodiments, the omeprazole or a pharmaceutically acceptable salt thereof is a 1:1 mixture, by weight, of micronized and non-micronized omeprazole or the pharmaceutically acceptable salt thereof. In some embodiments, the omeprazole or a pharmaceutically acceptable salt thereof is about a 1:2, 1:3, 1:4, 1:5, 1:6, 1:7, 1:8, or 1:9 mixture, by weight of micronized and non-micronized omeprazole or the pharmaceutically acceptable salt thereof. In some embodiments, the omeprazole or a pharmaceutically acceptable salt thereof is about a 1:2.3 mixture (i.e., about a 30:70 mixture) by weight of micronized and non-micronized omeprazole or the pharmaceutically acceptable salt thereof. In some embodiments, the omeprazole or a pharmaceutically acceptable salt thereof is about a 1:2, 1:3, 1:4, 1:5, 1:6, 1:7, 1:8, or 1:9 mixture, by weight of non-micronized and micronized omeprazole or the pharmaceutically acceptable salt thereof. In some embodiments, the omeprazole or a pharmaceutically acceptable salt thereof is about a 1:1.5 mixture (i.e., about a 40:60 mixture) by weight of non-micronized and micronized omeprazole or the pharmaceutically acceptable salt thereof.

In some embodiments, the first and second buffering agents are present in an amount sufficient to increase gastric fluid pH to a pH that prevents degradation of at least some of the PPI or a pharmaceutically acceptable salt of omeprazole in the gastric fluid.

In some embodiments, the first and second buffering agents provide a buffering capacity of from about 0.5 to about 4 mEq/ml dose of constituted storage-stable PPI system described herein with water. In some embodiments, the first and second buffering agents provide a buffering capacity of from about 1.6 to about 2.3 mEq/ml dose of constituted storage-stable PPI system described herein with water. In some embodiments, the first and second buffering agents provide a buffering capacity of about 2 mEq/ml dose of constituted storage-stable PPI system described herein with water. In some embodiments, the first and second buffering agents provide a buffering capacity of about 2.1 mEq/ml dose of constituted storage-stable PPI system described herein with water.

In some embodiments, the first and second buffering agents provide a buffering capacity of from about 0.5 to about 4 mEq/ml dose of constituted storage-stable omeprazole system described herein with water. In some embodiments, the first and second buffering agents provide a buffering capacity of from about 1.6 to about 2.3 mEq/ml dose of constituted storage-stable omeprazole system described herein with water. In some embodiments, the first and second buffering agents provide a buffering capacity of about 2 mEq/ml dose of constituted storage-stable omeprazole system described herein with water. In some embodiments, the first and second buffering agents provide a buffering capacity of about 2.1 mEq/ml dose of constituted storage-stable omeprazole system described herein with water.

In some embodiments, the first buffering agent and the second buffering agent can each independently comprise one buffering agent or a mixture of two or more buffering agents. In some embodiments, the first buffering agent and the second buffering agent each independently comprises 1, 2, 3, or 4 buffering agents. In some embodiments, the first buffering agent and the second buffering agent each independently comprises 1, 2, or 3 buffering agents. In some embodiments, the first buffering agent and the second buffering agent each independently comprises 1 buffering agent or 2 buffering agents.

In some embodiments, the first buffering agent and the second buffering agent are each independently selected from the group consisting of alkali metal or alkaline earth metal carbonates, bicarbonates, phosphates, citrates, borates, acetates, phthalates, tartrates, succinates, and mixtures thereof. In some embodiments, the first buffering agent and the second buffering agent are each independently selected from sodium or potassium carbonates, bicarbonates, phosphates, citrates, borates, acetates, phthalates, tartrates, succinates, and mixtures thereof.

In some embodiments, the first buffering agent is selected from sodium carbonate, sodium bicarbonate, sodium dihydrogen phosphate, sodium hydrogen phosphate, trisodium phosphate, sodium dihydrogen citrate, disodium hydrogen citrate, trisodium citrate, sodium tetraborate, sodium acetate, disodium hydrogen phthalate, sodium hydrogen phthalate, sodium bitartrate, disodium tartrate, sodium succinate, and mixtures thereof.

In some embodiments, the second buffering agent is selected from sodium and potassium carbonates, bicarbonates, phosphates, citrates, borates, acetates, phthalates, tartrates, succinates, and mixtures thereof.

In some embodiments, the first buffering agent and the second buffering agent are each independently selected from the group consisting of sodium bicarbonate, potassium bicarbonate, and a mixture thereof. In some embodiments, the first buffering agent is sodium bicarbonate. In some embodiments, the second buffering agent is a mixture of sodium bicarbonate and potassium bicarbonate. In some embodiments, the second mixture comprises about 11% sodium bicarbonate and about 89% potassium bicarbonate, by weight.

In some embodiments, the first mixture and the second mixture together comprise sodium bicarbonate and potassium bicarbonate at a ratio of about 1:100 to about 100:1 by weight. In some embodiments, the first mixture and the second mixture together comprise sodium bicarbonate and potassium bicarbonate at a ratio of about 1:2.5 to about 1:3.4 by weight. In some embodiments, sodium bicarbonate and potassium bicarbonate are present at a ratio of about 1:2.7 by weight.

In some embodiments, the first buffering agent and the second buffering agent are each independently selected from potassium carbonate, potassium bicarbonate, potassium dihydrogen phosphate, potassium hydrogen phosphate, tripotassium phosphate, potassium hydrogen citrate, dipotassium hydrogen citrate, tripotassium citrate, potassium tetraborate, potassium acetate, dipotassium hydrogen phthalate, potassium hydrogen phthalate, potassium bitartrate, dipotassium tartrate, potassium succinate, and a mixture thereof. In some embodiments, the first buffering agent and the second buffering agent are potassium bicarbonate.

Storage-stable PPI systems described herein (such as storage-stable omeprazole systems) can further comprise one or more pharmaceutically acceptable excipients including, but not limited to, sweeteners, flavoring agents, preservatives, thickening agents, suspending agents, opacifiers, disintegration agents, filling agents, surfactants, solubilizers, stabilizers, lubricants, diluents, and antifoaming agents.

Suitable sweeteners include, for example, mannitol, sucrose, fructose, dextrose, isomalt, maltitol, sorbitol, sucralose, acesulfame K, aspartame, cyclamate, saccharin, *stevia*, sucralose, sodium saccharin, xylitol, or a combination thereof. In some embodiments described herein, the sweetener is mannitol, sucralose, or maltitol, or a mixture thereof.

Suitable flavoring agents include, for example, the following flavors or mixtures thereof: mint, vanilla, banana, apple, orange, pear, peach, strawberry, raspberry, chocolate, lemon, lime, butterscotch, caramel, cherry, and cinnamon. In some embodiments described herein, the flavoring agent is mint flavor, vanilla flavor, or a mixture thereof.

Suitable preservatives include those that are suitable for use in pharmaceutical preparations, including antimicrobial preservatives. Suitable antimicrobial preservatives include, for example, sodium benzoate, potassium benzoate, calcium benzoate, methyl paraben sodium, ethyl paraben sodium, and mixtures thereof. In some embodiments described herein, the preservative is sodium benzoate, methyl paraben sodium, or a mixture thereof. In some embodiments, the preservative is a mixture of sodium benzoate and methyl paraben sodium.

Suitable thickening agents (or thickeners) include substances which can increase the viscosity of a liquid without substantially changing its other properties and which are suitable for oral pharmaceutical preparations. Examples of suitable thickeners include, for example, sodium alginate, xanthan gum, guar gum, and locust bean gum. In some embodiments, the thickener is sodium alginate, xanthan gum, or a mixture thereof.

Suitable opacifiers include pharmaceutically acceptable substances added to a material in order to make the ensuing system opaque, such as titanium dioxide ($TiO_2$).

In some embodiments, storage-stable PPI systems described herein (such as storage-stable-omeprazole systems) further comprise a sweetener, a flavoring agent, a preservative, or a mixture thereof.

In some embodiments, the second mixture in storage-stable PPI systems described herein (such as storage-stable omeprazole systems) further comprises a sweetener and a preservative.

In some embodiments, storage-stable PPI systems described herein (such as storage-stable omeprazole systems) are provided in a drug delivery device suitable for multi-dose administration of a PPI or a pharmaceutically acceptable salt thereof (such as omeprazole or a pharmaceutically acceptable salt thereof). In certain embodiments, the delivery device is as described in U.S. Pat. Nos. 9,051, 100, 10,238,803, or U.S. Patent Application Publication No. 2014/0311929, the contents of which are fully incorporated by reference.

In some embodiments, the delivery device is a PICS system. In some aspects, the PICS system is as shown in FIG. 1.

In some embodiments, the drug delivery device comprises two chambers. In some embodiments, the two chambers of the drug delivery device can be integrated. In some embodiments, the second chamber of the drug delivery device can be a container body (such as a bottle) and the first chamber can be a cap that can accommodate multi-particulate material and is mounted in the opening of the container body.

In some embodiments, the drug delivery device further comprises a means for releasing the contents of the first chamber into the second chamber without removing the cap from the drug delivery device.

In some embodiments, a storage-stable PPI system described herein (such as storage-stable omeprazole system) is provided in a container body comprising a cap, wherein (i) the container body contains the second mixture and has a container opening formed in an upper end thereof; (ii) the cap comprises a cylindrical accommodation portion comprising the first mixture and a cap portion sealing an upper end of the accommodation portion, and wherein (iii) the cap is mounted in the container opening of the container body, wherein when the cap is twisted, the first mixture is released into the container body. In some embodiments, the container body is an amber polyethylene terephthalate bottle and the cap is a polypropylene tamper evident cap.

In certain embodiments, a storage-stable PPI system (such as storage-stable omeprazole systems) described herein is formulated in a drug delivery device suitable for multi-dose administration of a PPI or a pharmaceutically acceptable salt thereof (such as omeprazole, or the pharmaceutically acceptable salt thereof), wherein the system comprises a therapeutically effective amount of the PPI or the pharmaceutically acceptable salt thereof (such as omeprazole or the pharmaceutically acceptable salt thereof), and wherein the system contains a percentage of moisture of no more than about 2.5%, and wherein the system contains no sodium from a sodium-containing buffering agent or the system contains sodium and potassium at a ratio of from about 1:100 to about 100:1 by weight, and further wherein the storage-stable omeprazole system is constituted with water prior to administration. In certain embodiments, the storage-stable PPI system contains sodium and potassium at a ratio of from about 1:50 to about 50:1 by weight. In certain embodiments, the storage-stable PPI system contains sodium and potassium at a ratio of from about 1:10 to about 10:1 by weight. In certain embodiments, the storage-stable PPI system contains sodium and potassium at a ratio of from about 1:2 to about 1:5 by weight. In certain embodiments, the storage-stable PPI system contains sodium and potassium at a ratio of from about 1:2.6 to about 1:3.4 by weight. In some embodiments of this aspect, the sodium and potassium are present at a ratio of about 1:3.2 by weight. In some embodiments, the storage-stable PPI system (such as a storage-stable omeprazole system) contains no sodium from a sodium-containing buffering agent.

In some embodiments, a storage-stable PPI system described herein (such as storage-stable omeprazole system) remains stable at 25° C./60% relative humidity for at least 2 years.

In some embodiments, the present disclosure provides a storage-stable omeprazole powder system, the system comprising (i) a first powder mixture comprising (a) a therapeutically effective amount of omeprazole, or a pharmaceutically acceptable salt thereof, (b) sodium alginate, and (c) a first buffering agent; and (ii) a second powder mixture comprising sodium alginate and a second buffering agent, wherein the first powder mixture and the second powder mixture are stored separately from each other and are mixed together on or just before constitution with water, and wherein the system contains sodium and potassium at a ratio of from about 1:2.6 to about 1:3.4 by weight.

In some embodiments, the omeprazole or the pharmaceutically acceptable salt thereof is micronized. In some embodiments, the omeprazole or the pharmaceutically acceptable salt thereof is a mixture of micronized and non-micronized omeprazole, or the pharmaceutically acceptable salt thereof. In some embodiments, the omeprazole or the pharmaceutically acceptable salt thereof comprises about 30 to about 70% micronized omeprazole, or the pharmaceutically acceptable salt thereof, and the rest of the omeprazole or the pharmaceutically acceptable salt thereof is non-micronized. In some embodiments, the omeprazole is a 1:1 mixture, by weight, of micronized and non-micronized omeprazole or the pharmaceutically acceptable salt thereof. In some embodiments, the omeprazole or a pharmaceutically acceptable salt thereof is about a 1:2, 1:3, 1:4, 1:5, 1:6, 1:7, 1:8, or 1:9 mixture, by weight of micronized and non-micronized omeprazole or the pharmaceutically acceptable salt thereof. In some embodiments, the omeprazole or a pharmaceutically acceptable salt thereof is about a 1:2.3 mixture (i.e., about a 30:70 mixture) by weight of micronized and non-micronized omeprazole or the pharmaceutically acceptable salt thereof. In some embodiments, the omeprazole or a pharmaceutically acceptable salt thereof is about a 1:2, 1:3, 1:4, 1:5, 1:6, 1:7, 1:8, or 1:9 mixture, by weight of non-micronized and micronized omeprazole or the pharmaceutically acceptable salt thereof. In some embodiments, the omeprazole or a pharmaceutically acceptable salt thereof is about a 1:1.5 mixture (i.e., about a 40:60 mixture) by weight of non-micronized and micronized omeprazole or the pharmaceutically acceptable salt thereof.

The first powder mixture can be prepared, for example, by wet granulation of a mixture of the omeprazole, or a pharmaceutically acceptable salt thereof, sodium alginate, and the first buffering agent, drying the granulates, and milling the dry granulates. In some embodiments, the first powder mixture further comprises dry sodium alginate. A suitable method for preparing the first powder mixture is described in, e.g., U.S. Pat. No. 8,093,271, the contents of which are fully incorporated by reference.

In some embodiments, about 20 to about 30% of the sodium alginate present in the first powder mixture are homogenously distributed over the surface of the first buffering agent. In some embodiments, about 20 to about 25% of the sodium alginate present in the first powder mixture are homogenously distributed over the surface of the first buffering agent. In some embodiments, the sodium alginate not distributed over the surface of the first buffering agent in the first powder mixture is dry, i.e., it contains a percentage of moisture of less than about 2%. In some embodiments, the sodium alginate present in the second powder mixture is dry.

In some embodiments, the dry sodium alginate has a moisture content of about 0.5% to about 1.5%. In some embodiments, the sodium alginate is low viscosity grade sodium alginate defined above.

The first buffering agent and the second buffering agents are present in an amount sufficient to increase gastric fluid pH to a pH that prevents degradation of at least some of the omeprazole, or the pharmaceutically acceptable salt thereof, in the gastric fluid. In some aspects, the first and second buffering agents provide a buffering capacity of from about 0.5 to about 4 mEq/ml dose of constituted storage-stable omeprazole powder system described herein with water. In some aspects, the first and second buffering agents provide a buffering capacity of from about 1.6 to about 2.3 mEq/ml dose of constituted storage-stable omeprazole powder system described herein with water. In some embodiments, the first and second buffering agents provide a buffering capacity of about 2 mEq/ml dose of constituted storage-stable omeprazole powder system described herein with water.

In some embodiments, the first and second buffering agents present in the storage-stable omeprazole powder system are each independently selected from the group consisting of alkali metal or alkaline earth metal carbonates, bicarbonates, phosphates, citrates, borates, acetates, phthalates, tartrates, succinates, and mixtures thereof. In some embodiments, the first and second buffering agents are each independently selected from the group consisting of sodium bicarbonate, potassium bicarbonate, and a mixture thereof.

In some embodiments, the first buffering agent in the storage-stable omeprazole powder system is sodium bicarbonate.

In some embodiments, the second buffering agent in the storage-stable omeprazole powder system is a mixture of sodium bicarbonate and potassium bicarbonate.

In some embodiments, the first buffering agent in the storage-stable omeprazole powder system is sodium bicarbonate and the second buffering agent is a mixture of sodium bicarbonate and potassium bicarbonate. In some embodiments, the second buffering agent is a mixture of about 11% sodium bicarbonate and about 89% potassium bicarbonate, by weight.

In some embodiments, the first powder mixture and the second powder mixture together in the storage-stable omeprazole powder system comprises sodium bicarbonate and potassium bicarbonate at a ratio of about 1:2.5 to about 1:3.4 by weight. In some embodiments, sodium bicarbonate and potassium bicarbonate are present at a ratio of about 1:2.7 by weight.

In some embodiments, the first buffering agent in the storage-stable omeprazole powder system is potassium bicarbonate and the second buffering agent is potassium bicarbonate.

In some embodiments, the second powder mixture of the storage-stable omeprazole powder system further comprises a sweetener and a preservative. Suitable sweeteners and preservatives as described above.

In some embodiments, the storage-stable omeprazole powder system is provided in a drug delivery device suitable for multi-dose administration of omeprazole.

In certain embodiments of this aspect, the drug delivery device comprises a first chamber comprising the first powder mixture and a second chamber comprising the second powder mixture. In certain embodiments, the first chamber and the second chamber can be integrated. In some embodiments, the second chamber of the drug delivery device can be a container body comprising the second powder mixture (such as a bottle) and the first chamber can be a cap comprising the first powder mixture which is mounted in the opening of the container body.

The drug delivery device can further comprise a means for releasing the first powder mixture into the second chamber without removing the cap from the drug delivery device.

In certain embodiments, the storage-stable omeprazole powder system is provided in a delivery device which is a container body comprising a cap. In some embodiments, (i) the container body contains the second powder mixture and has a container opening formed in an upper end thereof; (ii) the cap comprises a cylindrical accommodation portion comprising the first powder mixture and a cap portion sealing an upper end of the accommodation portion, wherein (iii) the cap is mounted in the container opening of the container body, wherein when the cap is twisted, the first powder mixture is released into the container body. In certain embodiments, the container body is an amber polyethylene terephthalate bottle and the cap is a polypropylene tamper evident cap.

In certain embodiments, the storage-stable omeprazole powder system of the present disclosure remains stable at 40° C./75% relative humidity for at least 6 months. In some embodiments, the storage-stable omeprazole powder system remains stable at 30° C./65% relative humidity for at least one year. In some embodiments, the storage-stable omeprazole powder system remains stable at 25° C./60% relative humidity for at least 2 years.

In some embodiments, the storage-stable PPI system (such as a storage-stable omeprazole system) described herein is enclosed within a sealed aluminium foil pouch to minimize ingress of moisture during storage of the un-constituted system. In some embodiments, the aluminium foil pouch may reduce moisture related degradation of the PPI or a pharmaceutically acceptable salt thereof (such as omeprazole or a pharmaceutically acceptable salt thereof) during storage of the storage-stable PPI system (such as storage-stable omeprazole system) described herein. In some embodiments, the aluminium foil pouch has a polymer coating inside. The aluminium foil pouches can be sealed by using a Hawo Heat Sealer (temperature setting 150° C., hold time of one to two seconds).

Oral Pharmaceutical Suspension

The present disclosure also provides an oral pharmaceutical suspension for providing a pharmaceutically effective amount of a PPI, or a pharmaceutically acceptable salt thereof, to a subject in need thereof, and especially for a pediatric subject. The oral pharmaceutical suspensions described herein contain sodium at acceptable levels for use in therapy in pediatric subjects. The oral pharmaceutical suspensions are specifically suitable for use in multi-dose dosage forms and are capable of providing uniform dosages of the PPI or the pharmaceutically acceptable salt thereof.

In one aspect, the present disclosure provides an oral pharmaceutical suspension, comprising water, a pharmaceutically effective amount of a PPI or a pharmaceutically acceptable salt thereof (such as omeprazole or a pharmaceutically acceptable salt thereof), dispersed in the water, and one of more buffering agents. In certain embodiments, the oral pharmaceutical suspension contains sodium and potassium at a ratio of from about 1:100 to about 100:1 by weight. In certain embodiments, the oral pharmaceutical suspension contains sodium and potassium at a ratio of from about 1:50 to about 50:1 by weight. In certain embodiments, the oral pharmaceutical suspension contains sodium and potassium at a ratio of from about 1:10 to about 10:1 by weight. In certain embodiments, the oral pharmaceutical suspension contains sodium and potassium at a ratio of from about 1:2 to about 1:5 by weight. In certain embodiments, the oral pharmaceutical suspension contains sodium and potassium at a ratio of from about 1:2.6 to about 1:3.4 by weight. In certain embodiments, the sodium and potassium are present in the oral pharmaceutical suspension at a ratio of about 1:3.2 by weight.

In some embodiments, the oral pharmaceutical suspension contains no sodium from a sodium-containing buffering agent such as sodium carbonate, sodium bicarbonate, sodium dihydrogen phosphate, sodium hydrogen phosphate, trisodium phosphate, sodium dihydrogen citrate, disodium hydrogen citrate, trisodium citrate, sodium tetraborate, sodium acetate, disodium hydrogen phthalate, sodium hydrogen phthalate, sodium bitartrate, disodium tartrate, and sodium succinate.

In some embodiments, oral pharmaceutical suspensions described herein further comprise a stabilizer or a thickener, or both. Suitable thickeners and stabilizers include gelling agents that stabilize liquid dosage forms, such as suspensions. In certain embodiments, the thickener or stabilizer is sodium alginate. In certain embodiments, the sodium alginate present is low viscosity grade sodium alginate described above.

In certain embodiments, about 1 ml of the oral pharmaceutical suspension contains from about 1 mg to about 10 mg of a PPI or a pharmaceutically acceptable salt thereof. In certain embodiments, about 1 ml of the oral pharmaceutical suspension contains from about 1 mg to about 10 mg of omeprazole, or a pharmaceutically acceptable salt thereof.

In certain embodiments, about 1 ml of the oral pharmaceutical suspension contains about 1 mg, about 2 mg, about 4 mg, or about 8 mg of a PPI or a pharmaceutically acceptable salt thereof. In certain embodiments, about 1 ml of the oral pharmaceutical suspension contains about 1 mg, about 2 mg, about 4 mg, or about 8 mg of omeprazole, or a pharmaceutically acceptable salt thereof.

In certain embodiments, about 1 ml of the oral pharmaceutical suspension contains about 2 mg or about 4 mg of a PPI, or a pharmaceutically acceptable salt thereof. In certain embodiments, about 1 ml of the oral pharmaceutical suspension contains about 2 mg or about 4 mg of omeprazole, or a pharmaceutically acceptable salt thereof.

In some embodiments, oral pharmaceutical suspensions described herein comprise 1, 2, 3, or 4 buffering agents. In some embodiments, oral pharmaceutical suspensions described herein comprise one buffering agent. In some embodiments, oral pharmaceutical suspensions described herein comprise 2 or 3 buffering agents. In some embodiments, oral pharmaceutical suspensions described herein comprise 2 buffering agents.

The oral pharmaceutical suspensions described herein, such as those comprising omeprazole or a pharmaceutically acceptable salt thereof, can comprise any suitable buffering agent that functions to substantially prevent or inhibit the acid degradation of the PPI or its pharmaceutically acceptable salt (such as omeprazole of a pharmaceutically acceptable salt thereof) by gastric acid sufficient to preserve the bioavailability of the PPI administered. In some embodiments, the one or more buffering agents are each independently selected from the group consisting of alkali metal or alkaline earth metal carbonates, bicarbonates, phosphates, citrates, borates, acetates, phthalates, tartrates, and succinates. In some embodiments, the one or more buffering agents are each independently selected from sodium or potassium carbonates, bicarbonates, phosphates, citrates, borates, acetates, phthalates, tartrates, and succinates.

In some embodiments, oral pharmaceutical suspensions described herein (such as suspensions comprising omeprazole or its salt) comprise at least one buffering agent selected from sodium carbonate, sodium bicarbonate, sodium dihydrogen phosphate, sodium hydrogen phosphate, trisodium phosphate, sodium dihydrogen citrate, disodium hydrogen citrate, trisodium citrate, sodium tetraborate, sodium acetate, disodium hydrogen phthalate, sodium hydrogen phthalate, sodium bitartrate, disodium tartrate, and sodium succinate. In some embodiments, oral pharmaceutical suspensions described herein comprise at least one buffering agent selected from potassium carbonate, potassium bicarbonate, potassium dihydrogen phosphate, potassium hydrogen phosphate, tripotassium phosphate, potassium dihydrogen citrate, dipotassium hydrogen citrate, tripotassium citrate, potassium tetraborate, potassium acetate, dipotassium hydrogen phthalate, potassium hydrogen phthalate, potassium bitartrate, dipotassium tartrate, and potassium succinate.

In some embodiments, oral pharmaceutical suspensions described herein (such as suspensions comprising omeprazole or a pharmaceutically acceptable salt thereof) comprise no more than one buffering agent selected from potassium carbonate, potassium bicarbonate, potassium dihydrogen phosphate, potassium hydrogen phosphate, tripotassium phosphate, potassium dihydrogen citrate, dipotassium hydrogen citrate, tripotassium citrate, potassium tetraborate, potassium acetate, dipotassium hydrogen phthalate, potassium hydrogen phthalate, potassium bitartrate, dipotassium tartrate, and potassium succinate. In some embodiments, the one buffering agent is potassium bicarbonate.

In some embodiments, oral pharmaceutical suspensions described herein (such as those comprising omeprazole or a pharmaceutically acceptable salt thereof) comprise two or more buffering agents selected from sodium and potassium carbonates, bicarbonates, phosphates, citrates, borates, acetates, phthalates, tartrates, and succinates. In some embodiments, oral pharmaceutical suspensions described herein comprise two buffering agents. In some embodiments, oral pharmaceutical suspensions described herein comprise both sodium bicarbonate and potassium bicarbonate.

In some embodiments, sodium bicarbonate and potassium bicarbonate are present in the oral pharmaceutical suspension at a ratio of about 1:2.5 to about 1:3.4 by weight per 1 ml of the suspension. In some embodiments, sodium bicarbonate and potassium bicarbonate are present at a ratio of about 1:2.7 by weight per 1 ml of the suspension.

In certain embodiments, oral pharmaceutical suspensions described herein contain sodium and potassium at a ratio of from about 1:100 to about 100:1 by weight. In certain embodiments, oral pharmaceutical suspensions described herein contain sodium and potassium at a ratio of from about 1:50 to about 50:1 by weight. In certain embodiments, oral pharmaceutical suspensions described herein contain sodium and potassium at a ratio of from about 1:10 to about 10:1 by weight. In certain embodiments, oral pharmaceutical suspensions described herein contain sodium and potassium at a ratio of from about 1:2 to about 1:5 by weight.

In certain embodiments, oral pharmaceutical suspensions described herein contain sodium and potassium at a ratio of from about 1:2.6 to about 1:3.4 by weight. In certain embodiments, the sodium and potassium are present in the oral pharmaceutical suspension at a ratio of about 1:3.2 by weight.

The one or more buffering agents present in the oral pharmaceutical suspensions described herein in an amount sufficient to increase gastric fluid pH to a pH that prevents degradation of at least some of the PPI (such as omeprazole or a pharmaceutically acceptable salt thereof) in the gastric fluid.

In certain embodiments, the one or more buffering agents present in the oral pharmaceutical suspension provide a buffering capacity of from about 0.5 to about 4 mEq per ml of the suspension. In certain embodiments, the one or more buffering agents present in the oral pharmaceutical suspension provide a buffering capacity of from about 1.6 to about 2.3 mEq per ml of the suspension. In certain embodiments, the one or more buffering agents present in the oral pharmaceutical suspension provide a buffering capacity of about 2 mEq per ml of the suspension.

In certain embodiments, oral pharmaceutical suspensions described herein contain low levels of sodium so that the suspensions are suitable for administration for pediatric subjects. In some aspects, oral pharmaceutical suspensions described herein comprise about 50 mg to about 150 mg of sodium per 5 ml of the suspension. In certain embodiments, about 70 mg to about 100 mg of sodium is present in 5 ml of suspension. In some embodiments, oral pharmaceutical suspensions described herein contain about 86 mg of sodium per 5 ml of the suspension. This 5 ml dose is equivalent to 4.3% of the WHO recommended maximum daily dietary intake of sodium for an adult.

In some embodiments, the PPI or a pharmaceutically acceptable salt thereof, such as omeprazole or a pharmaceutically acceptable salt thereof, present in the oral pharmaceutical suspensions described herein is micronized.

In some embodiments, the PPI or a pharmaceutically acceptable salt thereof is present in the oral pharmaceutical suspensions described herein, as a mixture of micronized and non-micronized PPI or a pharmaceutically acceptable salt thereof. In some embodiments of this aspect, the PPI or a pharmaceutically acceptable salt thereof comprises from about 30% to about 70% by weight micronized PPI or the pharmaceutically acceptable salt and the rest is non-micronized. In some embodiments, the PPI or a pharmaceutically acceptable salt thereof is a 1:1 mixture, by weight, of micronized and non-micronized PPI or the pharmaceutically acceptable salt thereof. In some embodiments, the PPI or a pharmaceutically acceptable salt thereof is about a 1:2, 1:3, 1:4, 1:5, 1:6, 1:7, 1:8, or 1:9 mixture, by weight of micronized and non-micronized PPI or the pharmaceutically acceptable salt thereof. In some embodiments, the PPI or a pharmaceutically acceptable salt thereof is about a 1:2.3 mixture (i.e., about a 30:70 mixture) by weight of micronized and non-micronized PPI or the pharmaceutically acceptable salt thereof. In some embodiments, the PPI or a pharmaceutically acceptable salt thereof is about a 1:2, 1:3, 1:4, 1:5, 1:6, 1:7, 1:8, or 1:9 mixture, by weight of non-micronized and micronized PPI or the pharmaceutically acceptable salt thereof. In some embodiments, the PPI or a pharmaceutically acceptable salt thereof is about a 1:1.5 mixture (i.e., about a 40:60 mixture) by weight of non-micronized and micronized PPI or the pharmaceutically acceptable salt thereof.

In some embodiments, the omeprazole or a pharmaceutically acceptable salt thereof present in the oral pharmaceutical suspensions described herein is a mixture of micronized and non-micronized omeprazole or a pharmaceutically acceptable salt thereof. In some embodiments, the omeprazole or a pharmaceutically acceptable salt thereof comprises from about 30% to about 70% by weight micronized omeprazole or the pharmaceutically acceptable salt and the rest is non-micronized. In some embodiments, the omeprazole or a pharmaceutically acceptable salt thereof is a 1:1 mixture, by weight, of micronized and non-micronized omeprazole or the pharmaceutically acceptable salt thereof. In some embodiments, the omeprazole or a pharmaceutically acceptable salt thereof is about a 1:2, 1:3, 1:4, 1:5, 1:6, 1:7, 1:8, or 1:9 mixture, by weight of micronized and non-micronized omeprazole or the pharmaceutically acceptable salt thereof. In some embodiments, the omeprazole or a pharmaceutically acceptable salt thereof is about a 1:2.3 mixture (i.e., about a 30:70 mixture) by weight of micronized and non-micronized omeprazole or the pharmaceutically acceptable salt thereof. In some embodiments, the omeprazole or a pharmaceutically acceptable salt thereof is about a 1:2, 1:3, 1:4, 1:5, 1:6, 1:7, 1:8, or 1:9 mixture, by weight of non-micronized and micronized omeprazole or the pharmaceutically acceptable salt thereof. In some embodiments, the omeprazole or a pharmaceutically acceptable salt thereof is about a 1:1.5 mixture (i.e., about a 40:60 mixture) by weight of non-micronized and micronized omeprazole or the pharmaceutically acceptable salt thereof.

In certain embodiments, the oral pharmaceutical suspension provides a biphasic pharmacokinetic profile having a first and second $C_{max}$ and a first and second $T_{max}$ following oral administration in a subject in need thereof.

In certain embodiments, a 5 ml dose of the oral pharmaceutical suspension described herein comprises about 10 mg or about 20 mg of a PPI or a pharmaceutically acceptable salt thereof (such as omeprazole or a pharmaceutically acceptable salt thereof), about 200 mg to about 300 mg sodium bicarbonate, about 600 mg to about 720 mg of potassium bicarbonate, and about 100 mg to about 150 mg of sodium alginate. In some embodiments, the 5 ml dose of the oral pharmaceutical suspension further comprises about 10 mg to about 15 mg methyl paraben sodium salt and about 15 mg to about 30 mg sodium benzoate.

In certain embodiments, a 5 ml dose of the oral pharmaceutical suspension described herein comprises about 10 mg or about 20 mg omeprazole, or a pharmaceutically acceptable salt thereof, about 256 mg sodium bicarbonate, about 695 mg of potassium bicarbonate, and about 125 mg of sodium alginate.

In some embodiments, the 5 ml dose of the oral pharmaceutical suspension further comprises about 11.45 mg methyl paraben sodium salt and about 25 mg sodium benzoate.

Oral pharmaceutical suspensions described herein (such as suspensions comprising omeprazole or a pharmaceutically acceptable salt thereof) can further comprise one or more pharmaceutically acceptable excipients including, but not limited to, sweeteners, flavoring agents, preservatives, thickening agents, suspending agents, opacifiers, disintegration agents, filling agents, surfactants, solubilizers, stabilizers, lubricants, diluents, and antifoaming agents.

Suitable sweeteners include, for example, mannitol, sucrose, fructose, dextrose, isomalt, maltitol, sorbitol, sucralose, acesulfame K, aspartame, cyclamate, saccharin, *stevia*, sucralose, sodium saccharin, xylitol, or a combination thereof. In some aspects described herein, the sweetener is mannitol, sucralose, or maltitol, or a mixture thereof.

Suitable flavoring agents include, for example, the following flavors or mixtures thereof: mint, vanilla, banana, apple, orange, pear, peach, strawberry, raspberry, chocolate, lemon, lime, butterscotch, caramel, cherry, and cinnamon. In some aspects described herein, the flavoring agent is mint flavor, vanilla flavor, or a mixture thereof.

Suitable preservatives include those that are suitable for use in pharmaceutical preparations, including antimicrobial preservatives. Suitable antimicrobial preservatives include, for example, sodium benzoate, potassium benzoate, calcium benzoate, methyl paraben sodium, ethyl paraben sodium, and mixtures thereof. In some aspects described herein, the preservative is sodium benzoate, methyl paraben sodium, or a mixture thereof. In some embodiments, the preservative is a mixture of sodium benzoate and methyl paraben sodium.

Suitable thickening agents (or thickeners) include substances which can increase the viscosity of a liquid without substantially changing its other properties and which are suitable for oral pharmaceutical preparations. Examples of suitable thickeners include, for example, sodium alginate, xanthan gum, guar gum, and locust bean gum. In some embodiments, the thickener is sodium alginate, xanthan gum, or a mixture thereof.

Suitable opacifiers include pharmaceutically acceptable substances added to a material in order to make the ensuing system opaque, such as titanium dioxide ($TiO_2$).

In some embodiments, oral pharmaceutical suspensions described herein further comprise a sweetener, a flavoring agent, a preservative, or a mixture thereof.

The oral pharmaceutical suspensions described herein remain stable for at least one month after constitution with water. The suspensions should be generally stored in a refrigerator (2° C.-8° C.). For up to 2 days, the suspensions can be stored below 25° C.

In some embodiments, the total amount of impurities (i.e., degradation products of the PPI, such as omeprazole) formed in the oral pharmaceutical suspension described herein on the day of constitution with water (i.e., on Day 0), after being stored at 40° C. and 75% relative humidity (RH) for 3 months before constitution with water, is not more than 0.16% w/w. In some embodiments, the total amount of impurities formed in the oral pharmaceutical suspension on Day 0 is not more than 0.11% w/w.

In some embodiments, the total amount of impurities formed in the oral pharmaceutical suspension described herein after being stored at 2° C.-8° C. for 28 days after being constituted with water (i.e., on Day 28), after being stored at 40° C. and 75% RH for 3 months before constitution with water, is not more than 0.28% w/w. In some embodiments, the total amount of impurities formed in the oral pharmaceutical suspension on Day 28 at 2° C.-8° C. is not more than 0.23% w/w.

In some embodiments, the total amount of impurities formed in the oral pharmaceutical suspension described herein after being stored at 2° C.-8° C. for 56 days after being constituted with water (i.e., on Day 56), after being stored at 40° C. and 75% RH for 3 months before constitution with water, is not more than 0.38% w/w. In some embodiments, the total amount of impurities formed in the oral pharmaceutical suspension on Day 56 at 2° C.-8° C. is not more than 0.33% w/w.

In some embodiments, sodium methyl parahydroxybenzoate is used as a preservative in the storage-stable PPI systems (such as storage-stable omeprazole systems) and oral pharmaceutical suspensions described herein. In some embodiments, the amount of sodium methyl parahydroxybenzoate present in the oral pharmaceutical suspension described herein on the day of constitution with water (i.e., on Day 0), after being stored at 40° C. and 75% RH for 3 months before constitution with water, is at least 94.5% w/w of the total amount originally present in the storage-stable PPI system described herein (such as a storage-stable omeprazole system). In some embodiments, the amount of sodium methyl parahydroxybenzoate present in the oral pharmaceutical suspension on Day 0 is at least 95.9% w/w of the total amount originally present in the storage-stable PPI system described herein (such as a storage-stable omeprazole system).

In some embodiments, the amount of sodium methyl parahydroxybenzoate present in the oral pharmaceutical suspension described herein after being stored at 2° C.-8° C. for 28 days after being constituted with water (i.e., on Day 28), after being stored at 40° C. and 75% RH for 3 months before constitution with water, is at least 92% w/w of the total amount originally present in the storage-stable PPI system described herein (such as a storage-stable omeprazole system). In some embodiments, the amount of sodium methyl parahydroxybenzoate present in the oral pharmaceutical suspension on Day 28 is at least 94% w/w of the total amount originally present in the storage-stable PPI system described herein (such as a storage-stable omeprazole system).

In some embodiments, the amount of sodium methyl parahydroxybenzoate present in the oral pharmaceutical suspension described herein after being stored at 2° C.-8° C. for 56 days after being constituted with water (i.e., on Day 56), after being stored at 40° C. and 75% RH for 3 months before constitution with water, is at least 84% w/w of the total amount originally present in the storage-stable PPI system described herein (such as a storage-stable omeprazole system). In some embodiments, the amount of sodium methyl parahydroxybenzoate present in the oral pharmaceutical suspension on Day 56 is at least 86.1% w/w of the total amount originally present in the storage-stable PPI system described herein (such as a storage-stable omeprazole system).

In some embodiments, oral pharmaceutical suspensions described herein are provided in a drug delivery device suitable for multi-dose administration of a PPI or a pharmaceutically acceptable salt thereof, such as omeprazole or a pharmaceutically acceptable salt thereof. Suitable drug delivery devices are, for example, as described above in connection with storage-stable systems described herein.

Methods of Treatment

Omeprazole, and other benzimidazole proton pump inhibitors, are well-known active substances for the treatment of acid-related disorders.

In one aspect, the present disclosure provides a method of inhibiting gastric acid secretion in a subject. The method comprises administering to a subject in need thereof an effective amount of an oral pharmaceutical suspension of the present disclosure described above.

In certain aspects, the present disclosure provides a method of inhibiting gastric acid secretion, comprising administering to a subject in need thereof an effective amount of an oral pharmaceutical suspension, wherein the oral pharmaceutical suspension comprises water, a pharmaceutically effective amount of a PPI or a pharmaceutically acceptable salt thereof, dispersed in the water, and one or more buffering agents, and wherein the suspension contains no sodium from a sodium-containing buffering agent or contains sodium and potassium at a ratio of from about 1:100 to about 100:1 by weight.

In certain embodiments, the present disclosure provides a method of inhibiting gastric acid secretion, comprising administering to a subject in need thereof an effective amount of an oral pharmaceutical suspension, wherein the oral pharmaceutical suspension comprises water, a pharmaceutically effective amount of omeprazole or a pharmaceutically acceptable salt thereof, dispersed in the water, and one or more buffering agents, and wherein the suspension contains no sodium from a sodium-containing buffering agent or contains sodium and potassium at a ratio of from about 1:100 to about 100:1 by weight.

In certain embodiments, the oral pharmaceutical suspension contains sodium and potassium at a ratio of from about 1:50 to about 50:1 by weight. In certain embodiments, the oral pharmaceutical suspension contains sodium and potassium at a ratio of from about 1:10 to about 10:1 by weight. In certain embodiments, the oral pharmaceutical suspension contains sodium and potassium at a ratio of from about 1:2 to about 1:5 by weight.

In certain embodiments, the present disclosure provides a method of inhibiting gastric acid secretion, comprising administering to a subject in need thereof an effective amount of an oral pharmaceutical suspension, wherein the oral pharmaceutical suspension comprises water, a pharmaceutically effective amount of a PPI or a pharmaceutically acceptable salt thereof, dispersed in the water, and one or more buffering agents, and wherein the suspension contains no sodium from a sodium-containing buffering agent or contains sodium and potassium at a ratio of from about 1:2.6 to about 1:3.4 by weight.

In certain embodiments, the present disclosure provides a method of inhibiting gastric acid secretion, comprising administering to a subject in need thereof an effective amount of an oral pharmaceutical suspension, wherein the oral pharmaceutical suspension comprises water, a pharmaceutically effective amount of omeprazole or a pharmaceutically acceptable salt thereof, dispersed in the water, and one or more buffering agents, and wherein the suspension contains no sodium from a sodium-containing buffering agent or contains sodium and potassium at a ratio of from about 1:2.6 to about 1:3.4 by weight.

In some embodiments, the oral pharmaceutical suspension contains no sodium from a sodium-containing buffering agent such as sodium carbonate, sodium bicarbonate, sodium dihydrogen phosphate, sodium hydrogen phosphate, trisodium phosphate, sodium dihydrogen citrate, disodium hydrogen citrate, trisodium citrate, sodium tetraborate, sodium acetate, disodium hydrogen phthalate, sodium hydrogen phthalate, sodium bitartrate, disodium tartrate, and sodium succinate.

In certain embodiments, the subject is a child. In some embodiments, the child is an infant, a toddler, a preadolescent, or an adolescent.

In some embodiments, the method comprises administering an oral pharmaceutical suspension described herein to the subject, wherein about 1 ml of the suspension contains from about 1 mg to about 10 mg of a PPI or a pharmaceutically acceptable salt thereof (such as omeprazole or a pharmaceutically acceptable salt thereof). In some embodiments, about 1 ml of the suspension contains about 1 mg, about 2 mg, about 4 mg or about 8 mg of a PPI or a pharmaceutically acceptable salt thereof (such as omeprazole or a pharmaceutically acceptable salt thereof). In some embodiments, about 1 ml of the suspension contains about 2 mg of a PPI or a pharmaceutically acceptable salt thereof (such as omeprazole or a pharmaceutically acceptable salt thereof). In some embodiments, about 1 ml of the suspension contains about 4 mg of a PPI or a pharmaceutically acceptable salt thereof (such as omeprazole or a pharmaceutically acceptable salt thereof).

Oral pharmaceutical suspensions described herein, and especially those containing omeprazole or a pharmaceutically acceptable salt thereof, are useful in the treatment of, for example, duodenal ulcers, gastric ulcers, NSAID-associated gastric and duodenal ulcers, reflux esophagitis, and symptomatic gastro-esophageal reflux disease (GERD).

In one aspect, the present disclosure also provides a method of inhibiting gastric acid secretion, comprising administering to a subject in need thereof an effective amount of an oral pharmaceutical suspension comprising water, a pharmaceutically effective amount of PPI or a pharmaceutically acceptable salt thereof (such as omeprazole, or a pharmaceutically acceptable salt thereof), dispersed in the water, and one or more buffering agents, wherein the suspension contains no sodium from a sodium-containing buffering agent or the suspension contains sodium and potassium at a ratio of from about 1:100 to about 100:1 by weight; and wherein the oral pharmaceutical suspension is prepared by combining a first mixture comprising (a) a therapeutically effective amount of a PPI or a pharmaceutically acceptable salt thereof (such as omeprazole, or a pharmaceutically acceptable salt thereof), wherein the first mixture contains a percentage of moisture of no more than about 2.5%; with a second mixture comprising a second buffering agent, wherein the second mixture contains a percentage of moisture of no more than about 2.5%; to obtain a combined mixture, wherein the combined mixture contains no sodium from a sodium-containing buffering agent or the combined mixture contains sodium and potassium at a ratio of from about 1:100 to about 100:1 by weight; and adding water to the combined mixture. In certain embodiments, the oral pharmaceutical suspension contains sodium and potassium at a ratio of from about 1:50 to about 50:1 by weight. In certain embodiments, the oral pharmaceutical suspension contains sodium and potassium at a ratio of from about 1:10 to about 10:1 by weight. In certain embodiments, the oral pharmaceutical suspension contains sodium and potassium at a ratio of from about 1:2 to about 1:5 by weight. In certain embodiments, the oral pharmaceutical suspension contains sodium and potassium at a ratio of from about 1:2.6 to about 1:3.4 by weight. In some embodiments, the second mixture further comprises a second desiccant.

In certain embodiments, the method of inhibiting gastric acid secretion comprises administering to a subject in need thereof an effective amount of an oral pharmaceutical suspension comprising water, a pharmaceutically effective amount of PPI, or a pharmaceutically acceptable salt thereof (such as omeprazole or a pharmaceutically acceptable salt thereof), dispersed in the water, and one or more buffering agents, wherein the suspension contains sodium and potassium at a ratio of from about 1:2.6 to about 1:3.4 by weight; and wherein the oral pharmaceutical suspension is prepared combining a first mixture comprising (a) a therapeutically effective amount of a PPI or a pharmaceutically acceptable salt thereof (such as omeprazole or a pharmaceutically acceptable salt thereof), wherein the first mixture contains a percentage of moisture of no more than about 2.5%; with a second mixture comprising a second desiccant and a second buffering agent; to obtain a combined mixture, wherein the combined mixture contains sodium and potassium at a ratio of from about 1:2.6 to about 1:3.4 by weight; and adding water to the combined mixture.

Dosage and Administration

In some aspects, an effective amount of the oral pharmaceutical suspension described herein is administered without food on an empty stomach, and preferably at least 30 minutes before a meal. A glass of water may be taken after taking a dose. Oral pharmaceutical suspensions described herein can also be administered to subjects via nasogastric (NG) or percutaneous endoscopic gastrostomy (PEG) tubes.

In some embodiments, oral pharmaceutical suspensions containing about 2 mg/ml of a PPI or a pharmaceutically acceptable salt (such as omeprazole or a pharmaceutically acceptable salt) are suitable for administering doses of less than about 15 mg.

In some embodiments, oral pharmaceutical suspensions containing about 4 mg/ml of a PPI or a pharmaceutically acceptable salt (such as omeprazole or a pharmaceutically acceptable salt) are suitable for administering doses of about 20 mg or about 40 mg.

A suitable dose for an adult is about 10 mg to about 40 mg once daily. In some aspects, the dose for an adult is about 10 mg, about 20 mg, about 30 mg or about 40 mg once daily.

The doses for children are generally based on their weight.

In some embodiments, a suitable dose of omeprazole or its salt, administered in an oral pharmaceutical suspension to a child of 1 month to 1 year of age, is about 1 mg/kg once daily.

In some embodiments, a suitable dose of omeprazole or its salt, administered in an oral pharmaceutical suspension to a child of more than 1 year of age weighing about 10-20 kg, is about 10 mg once daily. In some embodiments, this dose can be increased to 20 mg once daily.

In some embodiments, a suitable dose of omeprazole or its salt, administered in an oral pharmaceutical suspension to a child of more than 2 years of age and weighing more than about 20 kg, is about 20 mg once daily. In some embodiments, this dose can be increased to 40 mg once daily.

In some embodiments, oral pharmaceutical suspensions of the present disclosure can be used in combination with another pharmaceutical agent that is indicated for treating or preventing a gastrointestinal disorder, such as for example, an anti-bacterial agent, a prokinetic agent, a $H_2$-antagonist, and antacid, or sucralfate, which are commonly administered to minimize the pain and/or complications related to gastrointestinal disorders.

Methods of Preparing Oral Pharmaceutical Suspensions

In one aspect, the present disclosure provides a method of preparing an oral pharmaceutical suspension described herein. The method comprises combining a first mixture comprising (a) a therapeutically effective amount of a PPI or a pharmaceutically acceptable salt thereof (such as omeprazole, or a pharmaceutically acceptable salt thereof), wherein the first mixture contains a percentage of moisture of no more than about 2.5%; with a second mixture comprising a second buffering agent, wherein the second mixture contains a percentage of moisture of no more than about 2.5%; to obtain a combined mixture, wherein the combined mixture contains no sodium from a sodium-containing buffering agent or the combined mixture contains sodium and potassium at a ratio of from about 1:100 to about 100:1 by weight;

and adding water to the combined mixture. In certain embodiments, the combined mixture contains sodium and potassium at a ratio of from about 1:50 to about 50:1 by weight. In certain embodiments, the combined mixture contains sodium and potassium at a ratio of from about 1:10 to about 10:1 by weight. In certain embodiments, the combined mixture contains sodium and potassium at a ratio of from about 1:2 to about 1:5 by weight. In certain embodiments, the combined mixture contains sodium and potassium at a ratio of from about 1:2.6 to about 1:3.4 by weight. In some embodiments, the combined mixture contains sodium and potassium at a ratio of about 1:3.2 by weight. In some embodiments, the combined mixture contains no sodium from a sodium-containing buffering agent. In some embodiments, the first mixture and the second mixture independently has a moisture content of about 0.5% to about 1.5%. In some embodiments, the first mixture further comprises (b) a first desiccant and/or the second mixture further comprises a second desiccant.

In some embodiments, the present disclosure provides a method of preparing an oral pharmaceutical suspension, comprising combining a first mixture comprising (a) a therapeutically effective amount of a PPI or a pharmaceutically acceptable salt thereof (such as omeprazole or a pharmaceutically acceptable salt thereof), wherein the first mixture contains a percentage of moisture of no more than about 2.5%; with a second mixture comprising a second desiccant and a second buffering agent; to obtain a combined mixture, wherein the combined mixture contains sodium and potassium at a ratio of from about 1:2.6 to about 1:3.4 by weight; and adding water to the combined mixture. In some embodiments, the sodium and potassium are present at a ratio of about 1:3.2 by weight. In some embodiments, the first mixture has a moisture content of about 0.5% to about 1.5%.

In some embodiments, the first mixture further comprises (b) a first desiccant.

In some embodiments, the first desiccant and the second desiccant are sodium alginate.

In some embodiments, the first mixture further comprises (c) a first buffering agent.

In some embodiments, the first mixture and the second mixture are each independently in a form of a powder, a pellet, a granule, a seed, a bead, a spheroid, a microsphere, or a mixture thereof.

In some embodiments, the PPI or a pharmaceutically acceptable salt thereof (such as omeprazole or a pharmaceutically acceptable salt thereof) present in the oral pharmaceutical suspensions can be micronized before preparing the oral suspensions. Methods known in the art can be used for micronization of omeprazole or its salts. For example, traditional micronization techniques based on friction to reduce particle size can be used, such as milling, bashing and grinding. A typical industrial mill is composed of a cylindrical metallic drum that usually contains steel spheres. As the drum rotates the spheres inside collide with the particles of the solid, thus crushing them towards smaller diameters. In the case of grinding, the solid particles are formed when the grinding units of the device rub against each other while particles of the solid are trapped in between. Methods like crushing and cutting can also be used for reducing particle diameter. Crushing employs hammer-like tools to break the solid into smaller particles by means of impact. Cutting uses sharp blades to cut the rough solid pieces into smaller ones. In addition, modern micronization methods that use supercritical fluids in the micronization process can be used. These methods use supercritical fluids to induce a state of supersaturation, which leads to precipitation of individual particles. Suitable techniques include the RESS process (Rapid Expansion of Supercritical Solutions), the SAS method (Supercritical Anti-Solvent) and the PGSS method (Particles from Gas Saturated Solutions). These modern techniques allow for greater tunability of the process. Parameters like relative pressure and temperature, solute concentration, and antisolvent to solvent ratio can be varied to adjust to obtain the desired particle size. The supercritical fluid methods result in finer control over particle diameters, distribution of particle size and consistency of morphology.

In some embodiments, micronized PPI or its pharmaceutically acceptable salt suitable for use in the oral suspensions described herein is a composition where 90% or more of the particles have a particle size of 20 microns or less (i.e., ≤20 µm). In some embodiments, the oral pharmaceutical suspensions described herein comprise micronized PPI or a pharmaceutically acceptable salt thereof. In some embodiments, 90% or more of the particles in the micronized PPI or its salt have a particle size of 20 microns or less.

In some embodiments, micronized omeprazole or its pharmaceutically acceptable salt suitable for use in the oral suspensions described herein is a composition where 90% or more of the particles have a particle size of 20 microns or less (i.e., ≤20 µm). In some embodiments, the oral pharmaceutical suspensions described herein comprise micronized omeprazole. In some embodiments, 90% or more of the particles in the micronized omeprazole have a particle size of 20 microns or less.

In some embodiments, the non-micronized omeprazole is a composition where 95% or more of the particles have a particle size of 425 microns or less, and 30% or more of the particles have a particle size of 75 microns or less.

A PPI and its salts can be prepared by any suitable method known in the art.

Specifically, omeprazole and its salts can be prepared by any suitable method known in the art.

In some embodiments, the PPI or a pharmaceutically acceptable salt (such as omeprazole or a pharmaceutically acceptable salt thereof) used in the method described herein is micronized.

In some embodiments, the PPI or a pharmaceutically acceptable salt thereof is a mixture of micronized and non-micronized PPI, or the pharmaceutically acceptable salt thereof. In some embodiments, the PPI comprises about 30 to about 70% micronized PPI, or the pharmaceutically acceptable salt thereof, and the rest of the PPI, or the pharmaceutically acceptable salt thereof, is non-micronized. In some embodiments, the PPI is a 1:1 mixture, by weight, of micronized and non-micronized PPI, or the pharmaceutically acceptable salt thereof. In some embodiments, the PPI or a pharmaceutically acceptable salt thereof is about a 1:2, 1:3, 1:4, 1:5, 1:6, 1:7, 1:8, or 1:9 mixture, by weight of micronized and non-micronized PPI or the pharmaceutically acceptable salt thereof. In some embodiments, the PPI or a pharmaceutically acceptable salt thereof is about a 1:2.3 mixture (i.e., about a 30:70 mixture) by weight of micronized and non-micronized PPI or the pharmaceutically acceptable salt thereof. In some embodiments, the PPI or a pharmaceutically acceptable salt thereof is about a 1:2, 1:3, 1:4, 1:5, 1:6, 1:7, 1:8, or 1:9 mixture, by weight of non-micronized and micronized PPI or the pharmaceutically acceptable salt thereof. In some embodiments, the PPI or a pharmaceutically acceptable salt thereof is about a 1:1.5 mixture (i.e., about a 40:60 mixture) by weight of non-micronized and micronized PPI or the pharmaceutically acceptable salt thereof.

In some embodiments, omeprazole, or the pharmaceutically acceptable salt thereof, is a mixture of micronized and non-micronized omeprazole, or the pharmaceutically acceptable salt thereof. In some embodiments, the omeprazole comprises about 30 to about 70% micronized omeprazole, or the pharmaceutically acceptable salt thereof, and the rest of the omeprazole, or the pharmaceutically acceptable salt thereof, is non-micronized. In some embodiments, the omeprazole is a 1:1 mixture, by weight, of micronized and non-micronized omeprazole, or the pharmaceutically acceptable salt thereof. In some embodiments, the omeprazole or a pharmaceutically acceptable salt thereof is about a 1:2, 1:3, 1:4, 1:5, 1:6, 1:7, 1:8, or 1:9 mixture, by weight of micronized and non-micronized omeprazole or the pharmaceutically acceptable salt thereof. In some embodiments, the omeprazole or a pharmaceutically acceptable salt thereof is about a 1:2.3 mixture (i.e., about a 30:70 mixture) by weight of micronized and non-micronized omeprazole or the pharmaceutically acceptable salt thereof. In some embodiments, the omeprazole or a pharmaceutically acceptable salt thereof is about a 1:2, 1:3, 1:4, 1:5, 1:6, 1:7, 1:8, or 1:9 mixture, by weight of non-micronized and micronized omeprazole or the pharmaceutically acceptable salt thereof. In some embodiments, the omeprazole or a pharmaceutically acceptable salt thereof is about a 1:1.5 mixture (i.e., about a 40:60 mixture) by weight of non-micronized and micronized omeprazole or the pharmaceutically acceptable salt thereof.

The first buffering agent and the second buffering agent used in the present method are present in an amount sufficient to increase gastric fluid pH to a pH that prevents degradation of at least some of the omeprazole in the gastric fluid. In some aspects, the first and second buffering agents together provide a buffering capacity of from about 0.5 mEq/ml to about 4 mEq/ml dose of the suspension. In some aspects, the first and second buffering agents together provide a buffering capacity of from about 1.6 mEq/ml to about 2.3 mEq/ml dose of the suspension. In some aspects, the first and second buffering agents together provide a buffering capacity of about 2 mEq/ml dose of the suspension.

In some embodiments, the first buffering agent and the second buffering agent are each independently selected from the group consisting of alkali metal or alkaline earth metal carbonates, bicarbonates, phosphates, citrates, borates, acetates, phthalates, tartrates, and succinates. In some embodiments, the first buffering agent and the second buffering agent are each independently selected from the group consisting of sodium bicarbonate, potassium bicarbonate, and a mixture thereof.

In some embodiments, the first buffering agent is sodium bicarbonate. In other aspects, the second buffering agent is a mixture of sodium bicarbonate and potassium bicarbonate. In some embodiments, the second buffering agent comprises about 11% sodium bicarbonate and about 89% potassium bicarbonate, by weight.

In some embodiments, the first mixture and the second mixture together comprise sodium bicarbonate and potassium bicarbonate at a ratio of about 1:2.7 by weight.

In some embodiments, the first buffering agent and the second buffering agent are potassium bicarbonate.

In some embodiments, the second mixture further comprises a sweetener and a preservative.

In some embodiments, the method further comprises providing the oral pharmaceutical suspension in a drug delivery device suitable for multi-dose administration of a PPI or a pharmaceutically acceptable salt thereof (such as omeprazole or a pharmaceutically acceptable salt thereof). Suitable drug delivery devices are, for example, as described above in connection with storage-stable systems described herein.

The disclosure also provides the following particular embodiments:

Embodiment 1. A storage-stable omeprazole system, the system comprising a therapeutically effective amount of omeprazole, or a pharmaceutically acceptable salt thereof, wherein the system contains a percentage of moisture of no more than about 2.5%, and wherein the system contains no sodium from a sodium-containing buffering agent or the system contains sodium and potassium at a ratio of from about 1:2.6 to about 1:3.4 by weight, and further wherein the storage-stable omeprazole system is constituted with water prior to administration.

Embodiment 2. The storage-stable omeprazole system of Embodiment 1, wherein the sodium and potassium are present at a ratio of about 1:3.2 by weight.

Embodiment 3. The storage-stable omeprazole system of Embodiment 1 or 2, wherein the system has a moisture content of about 0.5% to about 1.5%.

Embodiment 4. The storage-stable omeprazole system of any of the preceding Embodiments, further comprising a pharmaceutically acceptable desiccant.

Embodiment 5. The storage-stable omeprazole system of Embodiment 4, wherein the pharmaceutically acceptable desiccant is sodium alginate.

Embodiment 6. The storage stable omeprazole system of Embodiment 5, wherein the sodium alginate is dry.

Embodiment 7. The storage-stable omeprazole system of Embodiment 6, wherein the dry sodium alginate has a moisture content of about 0.5% to about 1.5%.

Embodiment 8. The storage-stable omeprazole system of any one of Embodiments 5-7, wherein the sodium alginate is low viscosity grade sodium alginate.

Embodiment 9. The storage-stable omeprazole system of any of the preceding claims, wherein the system comprises one or more buffering agents each independently selected from the group consisting of alkali metal or alkaline earth metal carbonates, bicarbonates, phosphates, citrates, borates, acetates, phthalates, tartrates, and succinates.

Embodiment 10. The storage-stable omeprazole system of any one of Embodiments 1 and 3-9, wherein the system comprises one buffering agent which is potassium bicarbonate.

Embodiment 11. The storage-stable omeprazole system of Embodiment 9, wherein the system comprises two or more buffering agents selected from sodium and potassium carbonates, bicarbonates, phosphates, citrates, borates, acetates, phthalates, tartrates, and succinates.

Embodiment 12. The storage-stable omeprazole system of Embodiment 9 or 11, comprising sodium bicarbonate and potassium bicarbonate.

Embodiment 13. The storage-stable omeprazole system of Embodiment 12, wherein the sodium bicarbonate and potassium bicarbonate are present at a ratio of about 1:2.7 by weight.

Embodiment 14. The storage-stable omeprazole system of any one of preceding Embodiments, wherein the system is in a form of a powder, a pellet, a granule, a seed, a bead, a spheroid, a microsphere, or a mixture thereof.

Embodiment 15. A storage-stable omeprazole system, the system comprising (i) a first mixture comprising (a) a therapeutically effective amount of omeprazole, or a pharmaceutically acceptable salt thereof, wherein the first mixture contains a percentage of moisture of no more than about 2.5%; and (ii) a second mixture comprising a second buffering agent, wherein the second mixture contains a percentage of moisture of no more than about 2.5%, wherein the first mixture and the second mixture are stored separately from each other and are mixed together on or just before constitution with water, and wherein the system contains no sodium from a sodium-containing buffering agent or the system contains sodium and potassium at a ratio of from about 1:2.6 to about 1:3.4 by weight.

Embodiment 16. The storage-stable omeprazole system of Embodiment 15, wherein the sodium and potassium are present at a ratio of about 1:3.2 by weight.

Embodiment 17. The storage-stable omeprazole system of Embodiment 15 or 16, wherein the first mixture and/or the second mixture has a moisture content of about 0.5% to about 1.5%.

Embodiment 18. The storage-stable omeprazole system of any one of Embodiments 15-17, wherein the first mixture further comprises (b) a first desiccant and/or the second mixture further comprises a second desiccant.

Embodiment 19. The storage-stable omeprazole system of any one of Embodiments 15-18, wherein the first desiccant and the second desiccant are sodium alginate.

Embodiment 20. The storage-stable omeprazole system of any one of Embodiments 15-19, wherein the first mixture further comprises (c) a first buffering agent.

Embodiment 21. The storage-stable omeprazole system of any one of Embodiments 15-20, wherein the first mixture and the second mixture are each independently in a form of a powder, a pellet, a granule, a seed, a bead, a spheroid, a microsphere, or a mixture thereof.

Embodiment 22. The storage-stable omeprazole system of any one of Embodiments 1-21, wherein the omeprazole or the pharmaceutically acceptable salt thereof is micronized.

Embodiment 23. The storage-stable omeprazole system of any one of Embodiments 1-21, wherein the omeprazole or the pharmaceutically acceptable salt thereof is a mixture of micronized and non-micronized omeprazole or the pharmaceutically acceptable salt thereof.

Embodiment 24. The storage-stable omeprazole system of Embodiment 23, wherein the omeprazole, or the pharmaceutically acceptable salt thereof, comprises about 30 to about 70% micronized omeprazole, or the pharmaceutically acceptable salt thereof, and the rest of the omeprazole, or the pharmaceutically acceptable salt thereof, is non-micronized.

Embodiment 25. The storage-stable omeprazole system of Embodiment 24, wherein the omeprazole, or the pharmaceutically acceptable salt thereof, is a 1:1 mixture, by weight, of micronized and non-micronized omeprazole or the pharmaceutically acceptable salt thereof.

Embodiment 26. The storage-stable omeprazole system of any one of Embodiments 15-25, wherein the first buffering agent and the second buffering agent are present in an amount sufficient to increase gastric fluid pH to a pH that prevents degradation of at least some of the omeprazole in the gastric fluid.

Embodiment 27. The storage-stable omeprazole system of any one of Embodiments 20-26, wherein the first buffering agent and the second buffering agent together provide a buffering capacity of about 2 mEq/ml dose of constituted powder with water.

Embodiment 28. The storage-stable omeprazole system of any one of Embodiments 15-27, wherein the first buffering agent and the second buffering agent are each independently selected from the group consisting of alkali metal or alkaline earth metal carbonates, bicarbonates, phosphates, citrates, borates, acetates, phthalates, tartrates, succinates, and mixtures thereof.

Embodiment 29. The storage-stable omeprazole system of any one of Embodiments 14-28, wherein the first buffering agent and the second buffering agent are each independently selected from the group consisting of sodium bicarbonate, potassium bicarbonate, and a mixture thereof.

Embodiment 30. The storage-stable omeprazole system of any one of Embodiments 20-29, wherein the first buffering agent is sodium bicarbonate.

Embodiment 31. The storage-stable omeprazole system of any one of Embodiments 15-29, wherein the second buffering agent is a mixture of sodium bicarbonate and potassium bicarbonate.

Embodiment 32. The storage-stable omeprazole system of Embodiment 31, wherein the second buffering agent comprises about 11% sodium bicarbonate and about 89% potassium bicarbonate, by weight.

Embodiment 33. The storage-stable omeprazole system of any one of Embodiments 15-31, wherein the first mixture and the second mixture together comprise sodium bicarbonate and potassium bicarbonate at a ratio of about 1:2.7 by weight.

Embodiment 34. The storage-stable omeprazole system of any one of Embodiments 15-29, wherein the first buffering agent and the second buffering agent are potassium bicarbonate.

Embodiment 35. The storage-stable omeprazole system of any one of Embodiments 15-32 and 34, wherein the second mixture further comprises a sweetener and a preservative.

Embodiment 36. The storage-stable omeprazole system of any of the preceding Embodiments, wherein the storage-stable omeprazole system is provided in a drug delivery device suitable for multi-dose administration of omeprazole, or the pharmaceutically acceptable salt thereof.

Embodiment 37. The storage-stable omeprazole system of Embodiment 36, wherein the drug delivery device comprises two chambers.

Embodiment 38, The storage-stable omeprazole system of Embodiment 37, wherein the drug delivery device further comprises a means for releasing the contents of the first chamber into the second chamber without removing the cap from the drug delivery device.

Embodiment 39. The storage-stable omeprazole system of any one of Embodiments 15-38, wherein the storage-stable omeprazole system is provided in a container body comprising a cap, wherein (i) the container body contains the second mixture and has a container opening formed in an upper end thereof; (ii) the cap comprises a cylindrical accommodation portion comprising the first mixture and a cap portion sealing an upper end of the accommodation portion, and wherein (iii) the cap is mounted in the container opening of the container body, wherein when the cap is twisted, the first mixture is released into the container body.

Embodiment 40. The storage-stable omeprazole system of Embodiment 39, wherein the container body is an amber polyethylene terephthalate bottle and the cap is a polypropylene tamper evident cap.

Embodiment 41. The storage-stable omeprazole system of any one of the preceding Embodiments, wherein the powder system remains stable at 25° C./60% relative humidity for at least 2 years.

Embodiment 42. A storage-stable omeprazole system formulated in a drug delivery device suitable for multi-dose administration of omeprazole, or the pharmaceutically acceptable salt thereof, the system comprising a therapeutically effective amount of omeprazole, or a pharmaceutically acceptable salt thereof, wherein the system contains a percentage of moisture of no more than about 2.5%, and wherein the system contains no sodium from a sodium-containing buffering agent or the system contains sodium and potassium at a ratio of from about 1:2.6 to about 1:3.4 by weight, and further wherein the storage-stable omeprazole system is constituted with water prior to administration.

Embodiment 43. The storage-stable omeprazole system of any one of Embodiments 1-42, wherein the storage-stable omeprazole system is enclosed within a sealed aluminium foil pouch.

Embodiment 44. A storage-stable omeprazole powder system, the system comprising (i) a first powder mixture comprising (a) a therapeutically effective amount of omeprazole, or a pharmaceutically acceptable salt thereof, (b) sodium alginate, and (c) a first buffering agent; and (ii) a second powder mixture comprising sodium alginate and a second buffering agent, wherein the first powder mixture and the second powder mixture are stored separately from each other and are mixed together on or just before constitution with water, and wherein the system contains sodium and potassium at a ratio of from about 1:2.6 to about 1:3.4 by weight.

Embodiment 45. The storage-stable omeprazole powder system of Embodiment 44, wherein the omeprazole or the pharmaceutically acceptable salt thereof is micronized.

Embodiment 46. The storage-stable omeprazole powder system of Embodiment 44 or 45, wherein the omeprazole or the pharmaceutically acceptable salt thereof is a mixture of micronized and non-micronized omeprazole, or the pharmaceutically acceptable salt thereof.

Embodiment 47. The storage-stable omeprazole powder system of Embodiment 46, wherein the omeprazole or the pharmaceutically acceptable salt thereof comprises about 30 to about 70% micronized omeprazole, or the pharmaceutically acceptable salt thereof, and the rest of the omeprazole or the pharmaceutically acceptable salt thereof is non-micronized.

Embodiment 48. The storage-stable omeprazole powder system of Embodiment 46, wherein the omeprazole is a 1:1 mixture, by weight, of micronized and non-micronized omeprazole or the pharmaceutically acceptable salt thereof.

Embodiment 49. The storage-stable omeprazole powder system of any one of Embodiments 44-48, wherein the omeprazole, or the pharmaceutically acceptable salt thereof, and about 20 to about 30% of the sodium alginate present in the first powder mixture are homogenously distributed over the surface of the first buffering agent.

Embodiment 50. The storage-stable omeprazole powder system of Embodiment 49, wherein the omeprazole, or the pharmaceutically acceptable salt thereof, and about 20 to about 25% of the sodium alginate present in the first powder mixture are homogenously distributed over the surface of the first buffering agent.

Embodiment 51. The storage-stable omeprazole powder system of Embodiment 49 or 50, wherein the sodium alginate not distributed over the surface of the first buffering agent in the first powder mixture is dry.

Embodiment 52. The storage-stable omeprazole powder system of any one of Embodiments 44-51, wherein the sodium alginate present in the second powder mixture is dry.

Embodiment 53. The storage-stable omeprazole powder system of Embodiment 51 or 52, wherein the dry sodium alginate has a moisture content of about 0.5% to about 1.5%.

Embodiment 54. The storage-stable omeprazole powder system of any one of Embodiments 44-53, wherein the sodium alginate is low viscosity grade sodium alginate.

Embodiment 55. The storage-stable omeprazole powder system of any one of Embodiments 44-54, wherein the first and second buffering agents are present in an amount sufficient to increase gastric fluid pH to a pH that prevents degradation of at least some of the omeprazole, or the pharmaceutically acceptable salt thereof, in the gastric fluid.

Embodiment 56. The storage-stable omeprazole powder system of any one of Embodiments 44-55, wherein the first and second buffering agents together provide a buffering capacity of about 2 mEq/ml dose of constituted powder with water.

Embodiment 57. The storage-stable omeprazole powder system of any one of Embodiments 44-56, wherein the first and second buffering agents are each independently selected from the group consisting of alkali metal or alkaline earth metal carbonates, bicarbonates, phosphates, citrates, borates, acetates, phthalates, tartrates, succinates, and mixtures thereof.

Embodiment 58. The storage-stable omeprazole powder system of any one of Embodiments 44-57, wherein the first and second buffering agents are each independently selected from the group consisting of sodium bicarbonate, potassium bicarbonate, and a mixture thereof.

Embodiment 59. The storage-stable omeprazole powder system of any one of Embodiments 44-58, wherein the first buffering agent is sodium bicarbonate.

Embodiment 60. The storage-stable omeprazole powder system of any one of Embodiments 44-59, wherein the second buffering agent is a mixture of sodium bicarbonate and potassium bicarbonate.

Embodiment 61. The storage-stable omeprazole powder system of Embodiment 60, wherein the mixture comprises about 11% sodium bicarbonate and about 89% potassium bicarbonate, by weight.

Embodiment 62. The storage-stable omeprazole powder system of any one of Embodiments 44-61, wherein the first powder mixture and the second powder mixture together comprise sodium bicarbonate and potassium bicarbonate at a ratio of about 1:2.7 by weight.

Embodiment 63. The storage-stable omeprazole powder system of any one of Embodiments 44-62, wherein the second powder mixture further comprises a sweetener and a preservative.

Embodiment 64. The storage-stable omeprazole powder system of any one of Embodiments 44-63, wherein the storage-stable omeprazole powder system is provided in a drug delivery device suitable for multi-dose administration of omeprazole.

Embodiment 65. The storage-stable omeprazole powder system of Embodiment 64, wherein the drug delivery device comprises a first chamber comprising the first powder mixture and a second chamber comprising the second powder mixture.

Embodiment 66. The storage-stable omeprazole powder system of Embodiment 65, wherein the drug delivery device further comprises a means for releasing the first powder mixture into the second chamber without removing the cap from the drug delivery device.

Embodiment 67. The storage-stable omeprazole powder system of any one of Embodiments 44-66, wherein the storage-stable omeprazole powder system is provided in a container body comprising a cap, wherein (i) the container body contains the second powder mixture and has a container opening formed in an upper end thereof; (ii) the cap comprises a cylindrical accommodation portion comprising the first powder mixture and a cap portion sealing an upper end of the accommodation portion, and wherein (iii) the cap is mounted in the container opening of the container body, wherein when the cap is twisted, the first powder mixture is released into the container body.

Embodiment 68. The storage-stable omeprazole powder system of Embodiment 67, wherein the container body is an amber polyethylene terephthalate bottle and the cap is a polypropylene tamper evident cap.

Embodiment 69. The storage-stable omeprazole powder system of any one of Embodiments 44-68, wherein the powder system remains stable at 25° C./60% relative humidity for at least 2 years.

Embodiment 70. The storage-stable omeprazole powder system of any one of Embodiments 44-69, wherein the storage-stable omeprazole system is enclosed within a sealed aluminium foil pouch.

Embodiment 71. An oral pharmaceutical suspension, comprising water, a pharmaceutically effective amount of omeprazole, or a pharmaceutically acceptable salt thereof, dispersed in the water, and one or more buffering agents, and wherein the suspension contains no sodium from a sodium-containing buffering agent or the suspension contains sodium and potassium at a ratio of from about 1:2.6 to about 1:3.4 by weight.

Embodiment 72. The oral pharmaceutical suspension of Embodiment 71, further comprising sodium alginate.

Embodiment 73. The oral pharmaceutical suspension of Embodiment 71 or 72, wherein about 1 ml of the suspension contains from about 1 mg to about 10 mg of omeprazole, or the pharmaceutically acceptable salt thereof.

Embodiment 74. The oral pharmaceutical suspension of Embodiment 73, wherein about 1 ml of the suspension contains about 1 mg, about 2 mg, about 4 mg, or about 8 mg of omeprazole, or the pharmaceutically acceptable salt thereof.

Embodiment 75. The oral pharmaceutical suspension of Embodiment 74, wherein about 1 ml of the suspension contains about 2 mg or about 4 mg of omeprazole, or the pharmaceutically acceptable salt thereof.

Embodiment 76. The oral pharmaceutical suspension of any one of Embodiments 71-75, wherein the one or more buffering agents provide a buffering capacity of about 2 mEq per ml of the suspension.

Embodiment 77. The oral pharmaceutical suspension of any one of Embodiments 71-76, wherein the one or more buffering agents are each independently selected from the group consisting of alkali metal or alkaline earth metal carbonates, bicarbonates, phosphates, citrates, borates, acetates, phthalates, tartrates, and succinates.

Embodiment 78. The oral pharmaceutical suspension of any one of Embodiments 71-77, comprising one buffering agent.

Embodiment 79. The oral pharmaceutical suspension of Embodiment 78, wherein the one buffering agent is potassium bicarbonate.

Embodiment 80. The oral pharmaceutical suspension of any one of Embodiments 71-77, comprising a mixture of two buffering agents.

Embodiment 81. The oral pharmaceutical suspension of Embodiment 80, comprising a mixture of sodium bicarbonate and potassium bicarbonate at a ratio of about 1:2.7 by weight.

Embodiment 82. The oral pharmaceutical suspension of any one of Embodiments 71-77 and 80-81, wherein the suspension comprises about 86 mg of sodium per 5 ml of the suspension.

Embodiment 83. The oral pharmaceutical suspension of any one of Embodiments 71-77 and 80-82, wherein the sodium and potassium are present at a ratio of about 1:3.2 by weight.

Embodiment 84. The oral pharmaceutical suspension of any one of Embodiments 71-83, wherein the suspension provides a biphasic pharmacokinetic profile having a first and second $C_{max}$ and a first and second $T_{max}$ following oral administration in a subject in need thereof.

Embodiment 85. The oral pharmaceutical suspension of any of Embodiments 66-77, wherein a 5 ml dose comprises about 10 mg or about 20 mg omeprazole, or the pharmaceutically acceptable salt thereof, about 256 mg sodium bicarbonate, about 695 mg of potassium bicarbonate, and about 125 mg of sodium alginate.

Embodiment 86. The oral pharmaceutical suspension of Embodiment 78, further comprising about 11.45 mg methyl paraben sodium salt and about 25 mg sodium benzoate.

Embodiment 87. The oral pharmaceutical suspension of any one of Embodiments 71-86, wherein the omeprazole or the pharmaceutically acceptable salt thereof is micronized.

Embodiment 88. The oral pharmaceutical suspension of any one of Embodiments 71-86, wherein the omeprazole or the pharmaceutically acceptable salt thereof is a mixture of micronized and non-micronized omeprazole, or the pharmaceutically acceptable salt thereof.

Embodiment 89. The oral pharmaceutical suspension of Embodiment 88, wherein the omeprazole or the pharmaceutically acceptable salt thereof comprises about 30 to about 70% micronized omeprazole, or the pharmaceutically acceptable salt thereof, and the rest of the omeprazole or the pharmaceutically acceptable salt thereof is non-micronized.

Embodiment 90. The oral pharmaceutical suspension of Embodiment 88, wherein the omeprazole is a 1:1 mixture, by weight, of micronized and non-micronized omeprazole or the pharmaceutically acceptable salt thereof.

Embodiment 91. The oral pharmaceutical suspension of any one of Embodiments 71-90, wherein the suspension is provided in a drug delivery device suitable for multi-dose administration of omeprazole.

Embodiment 92. A method of inhibiting gastric acid secretion, comprising administering to a subject in need thereof an effective amount of the oral pharmaceutical suspension of any one of Embodiments 71-91.

Embodiment 93. The method of Embodiment 92, wherein the subject is a child.

Embodiment 94. The method of Embodiment 93, wherein the child is an infant, a toddler, a preadolescent, or an adolescent.

Embodiment 95. The method of any one of Embodiments 92-94, wherein about 1 ml of the suspension contains from about 1 mg to about 10 mg of omeprazole, or the pharmaceutically acceptable salt thereof.

Embodiment 96. The method of any one of Embodiments 92-95, wherein 1 ml of the suspension contains about 1 mg, about 2 mg, about 4 mg or about 8 mg of omeprazole, or the pharmaceutically acceptable salt thereof.

Embodiment 97. The method of any one of Embodiments 92-96, wherein 1 ml of the suspension contains about 2 mg of omeprazole, or the pharmaceutically acceptable salt thereof.

Embodiment 98. The method of any one of Embodiments 92-96, wherein 1 ml of the suspension contains about 4 mg of omeprazole, or the pharmaceutically acceptable salt thereof.

Embodiment 99. A method of preparing an oral pharmaceutical suspension, comprising combining a first mixture comprising (a) a therapeutically effective amount of omeprazole, or a pharmaceutically acceptable salt thereof, wherein the first mixture contains a percentage of moisture of no more than about 2.5%; with a second mixture comprising a second buffering agent, wherein the second mixture contains a percentage of moisture of no more than about 2.5%; to obtain a combined mixture, wherein the combined mixture contains no sodium from a sodium-containing buffering agent or the combined mixture contains sodium and potassium at a ratio of from about 1:2.6 to about 1:3.4 by weight; and adding water to the combined mixture.

Embodiment 100. The method of Embodiment 99, wherein the sodium and potassium are present at a ratio of about 1:3.2 by weight.

Embodiment 101. The method of Embodiment 99 or 100, wherein the first mixture has a moisture content of about 0.5% to about 1.5%.

Embodiment 102. The method of any one of Embodiments 99-101, wherein the first mixture further comprises (b) a first desiccant and/or the second mixture further comprises a second desiccant.

Embodiment 103. The method of any one of Embodiments 99-102, wherein the first desiccant and the second desiccant are sodium alginate.

Embodiment 104. The method of any one of Embodiments 99-103, wherein the first mixture further comprises (c) a first buffering agent.

Embodiment 105. The method of any one of Embodiments 99-104, wherein the first mixture and the second mixture are each independently in a form of a powder, a pellet, a granule, a seed, a bead, a spheroid, a microsphere, or a mixture thereof.

Embodiment 106. The method of any one of Embodiments 99-105, wherein the omeprazole, or the pharmaceutically acceptable salt thereof, is micronized.

Embodiment 107. The method of any one of Embodiments 99-105, wherein the omeprazole, or the pharmaceutically acceptable salt thereof, is a mixture of micronized and non-micronized omeprazole, or the pharmaceutically acceptable salt thereof.

Embodiment 108. The method of Embodiment 107, wherein the omeprazole comprises about 30 to about 70% micronized omeprazole, or the pharmaceutically acceptable salt thereof, and the rest of the omeprazole, or the pharmaceutically acceptable salt thereof, is non-micronized.

Embodiment 109. The method of Embodiment 107, wherein the omeprazole is a 1:1 mixture, by weight, of micronized and non-micronized omeprazole, or the pharmaceutically acceptable salt thereof.

Embodiment 110. The method of any one of Embodiments 99-109, wherein the first buffering agent and the second buffering agent are present in an amount sufficient to increase gastric fluid pH to a pH that prevents degradation of at least some of the omeprazole in the gastric fluid.

Embodiment 111. The method of any one of Embodiments 104-110, wherein the first buffering agent and the second buffering agent together provide a buffering capacity of about 2 mEq/ml dose of the suspension.

Embodiment 112. The method of any one of Embodiments 99-111, wherein the first buffering agent and the second buffering agent are each independently selected from the group consisting of alkali metal or alkaline earth metal carbonates, bicarbonates, phosphates, citrates, borates, acetates, phthalates, tartrates, and succinates.

Embodiment 113. The method of any one of Embodiments 99-112, wherein the first buffering agent and the second buffering agent are each independently selected from the group consisting of sodium bicarbonate, potassium bicarbonate, and a mixture thereof.

Embodiment 114. The method of any one of Embodiments 104-113, wherein the first buffering agent is sodium bicarbonate.

Embodiment 115. The method of any one of Embodiments 99-113, wherein the second buffering agent is a mixture of sodium bicarbonate and potassium bicarbonate.

Embodiment 116. The method of Embodiment 115, wherein the mixture comprises about 11% sodium bicarbonate and about 89% potassium bicarbonate, by weight.

Embodiment 117. The method of any one of Embodiments 99-116, wherein the first mixture and the second mixture together comprise sodium bicarbonate and potassium bicarbonate at a ratio of about 1:2.7 by weight.

Embodiment 118. The method of any one of Embodiments 99 and 101-113, wherein the first buffering agent and the second buffering agent are potassium bicarbonate.

Embodiment 119. The method of any one of Embodiments 99-118, wherein the second mixture further comprises a sweetener and a preservative.

Embodiment 120. The method of any one of Embodiments 99-119, wherein the oral pharmaceutical suspension is provided in a drug delivery device suitable for multi-dose administration of omeprazole.

Embodiment 121. A method of inhibiting gastric acid secretion, comprising administering to a subject in need thereof an effective amount of an oral pharmaceutical suspension comprising water, a pharmaceutically effective amount of omeprazole, or a pharmaceutically acceptable salt thereof, dispersed in the water, and one or more buffering agents, wherein the suspension contains no sodium from a sodium-containing buffering agent or the suspension contains sodium and potassium at a ratio of from about 1:2.6 to about 1:3.4 by weight; and wherein the oral pharmaceutical suspension is prepared as claimed in any one of Embodiments 99-120.

Embodiment 122. The oral pharmaceutical suspension of any one of Embodiments 71-90, wherein the suspension remains stable for at least one month at 2° C.-8° C. after constitution with water.

The disclosure also provides the following particular embodiments:

Embodiment I. A storage-stable omeprazole system, the system comprising a therapeutically effective amount of omeprazole, or a pharmaceutically acceptable salt thereof, wherein the system contains a percentage of moisture of no more than about 2.5%, and wherein the system contains no sodium from a sodium-containing buffering agent or the system contains sodium and potassium at a ratio of from about 1:2.6 to about 1:3.4 by weight, and further wherein the storage-stable omeprazole system is constituted with water prior to administration.

Embodiment II. The storage-stable omeprazole system of Embodiment I, wherein the system comprises one or more buffering agents each independently selected from the group consisting of alkali metal or alkaline earth metal carbonates, bicarbonates, phosphates, citrates, borates, acetates, phthalates, tartrates, and succinates.

Embodiment III. The storage-stable omeprazole system of Embodiment I, the system comprising (i) a first mixture comprising (a) a therapeutically effective amount of omeprazole, or a pharmaceutically acceptable salt thereof, wherein the first mixture contains a percentage of moisture of no more than about 2.5%; and (ii) a second mixture comprising a second buffering agent, wherein the second mixture contains a percentage of moisture of no more than about 2.5%, wherein the first mixture and the second mixture are stored separately from each other and are mixed together on or just before constitution with water, and wherein the system contains no sodium from a sodium-containing buffering agent or the system contains sodium and potassium at a ratio of from about 1:2.6 to about 1:3.4 by weight.

Embodiment IV. A storage-stable omeprazole powder system, the system comprising (i) a first powder mixture comprising (a) a therapeutically effective amount of omeprazole, or a pharmaceutically acceptable salt thereof, (b) sodium alginate, and (c) a first buffering agent; and (ii) a second powder mixture comprising sodium alginate and a second buffering agent, wherein the first powder mixture and the second powder mixture are stored separately from each other and are mixed together on or just before constitution with water, and wherein the system contains sodium and potassium at a ratio of from about 1:2.6 to about 1:3.4 by weight.

Embodiment V. The storage-stable omeprazole system or the storage-stable omeprazole powder system of any one of Embodiments I-IV, wherein the omeprazole or the pharmaceutically acceptable salt thereof is micronized.

Embodiment VI. The storage-stable omeprazole system or the storage-stable omeprazole powder system of any one of Embodiments I-IV, wherein the omeprazole or the pharmaceutically acceptable salt thereof is a mixture of micronized and non-micronized omeprazole or the pharmaceutically acceptable salt thereof.

Embodiment VII. The storage-stable omeprazole system or the storage-stable omeprazole powder system of any of the preceding claims, wherein the storage-stable omeprazole system or the omeprazole powder system is provided in a drug delivery device suitable for multi-dose administration of omeprazole, or the pharmaceutically acceptable salt thereof.

Embodiment VIII. The storage-stable omeprazole powder system of Embodiment IV or VII, wherein the storage-stable omeprazole powder system is provided in a container body comprising a cap, wherein (i) the container body contains the second powder mixture and has a container opening formed in an upper end thereof; (ii) the cap comprises a cylindrical accommodation portion comprising the first powder mixture and a cap portion sealing an upper end of the accommodation portion, and wherein (iii) the cap is mounted in the container opening of the container body, wherein when the cap is twisted, the first powder mixture is released into the container body.

Embodiment IX. The storage-stable omeprazole system or the storage-stable omeprazole powder system of any one of the preceding claims, wherein the omeprazole system or the omeprazole powder system remains stable at 25° C./60% relative humidity for at least 2 years.

Embodiment X. An oral pharmaceutical suspension, comprising water, a pharmaceutically effective amount of omeprazole, or a pharmaceutically acceptable salt thereof, dispersed in the water, and one or more buffering agents, and wherein the suspension contains no sodium from a sodium-containing buffering agent or the suspension contains sodium and potassium at a ratio of from about 1:2.6 to about 1:3.4 by weight.

Embodiment XI. The oral pharmaceutical suspension of Embodiment X, wherein about 1 ml of the suspension contains from about 1 mg to about 10 mg of omeprazole, or the pharmaceutically acceptable salt thereof.

Embodiment XII. The oral pharmaceutical suspension of Embodiment X or XI, wherein the suspension remains stable for at least one month at 2° C.-8° C. after constitution with water.

Embodiment XIII. A method of inhibiting gastric acid secretion, comprising administering to a subject in need thereof an effective amount of the oral pharmaceutical suspension of any one of Embodiments X-XII.

Embodiment XIV. A method of administering an oral pharmaceutical suspension to a subject in need of inhibition of gastric acid secretion, said method comprising 1) preparing an oral pharmaceutical suspension, comprising combining a first mixture comprising a therapeutically effective amount of omeprazole, or a pharmaceutically acceptable salt thereof, wherein the first mixture contains a percentage of moisture of no more than about 2.5%; with a second mixture comprising a second buffering agent, wherein the second mixture contains a percentage of moisture of no more than about 2.5%; to obtain a combined mixture, wherein the combined mixture contains no sodium from a sodium-containing buffering agent or the combined mixture contains sodium and potassium at a ratio of from about 1:2.6 to about 1:3.4 by weight; and adding water to the combined mixture; and 2) administering to the subject in need thereof an effective amount of the oral pharmaceutical suspension.

Embodiment XV. The method of Embodiment XIII or XIV, wherein the subject is a child.

EXAMPLES

The formulations described herein is now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Example 1

Exemplary Formulation and Manufacturing Details of Omeprazole 2 mg/ml and 4 mg/ml Oral Suspensions and Storage-Stable Omeprazole Powder Systems In the Table 1 below, the granulate composition is used in the preparation of an example of the first mixture present in the storage-stable omeprazole powder systems described herein.

TABLE 1

| Omeprazole Oral Susp'n | Example A | Example B | Example C |
| --- | --- | --- | --- |
| Constituted Susp'n Composition | mg/ml | mg/ml | mg/ml |
| Omeprazole | 2 | 4 | 4 |
| Sodium Bicarbonate | 51.2 | 51.2 | 51.2 |
| Potassium Bicarbonate | 139 | 139 | 139 |
| Sodium Alginate | 1.17 | 1.17 | 1.17 |

TABLE 1-continued

| Omeprazole Oral Susp'n | Example A | Example B | Example C |
|---|---|---|---|
| Mannitol | 4.99 | 5.00 | 4.99 |
| Sucralose | 3.99 | 3.99 | 3.99 |
| Sodium Alginate (Dried) | 23.8 | 23.8 | 23.8 |
| Xanthan Gum | 2.86 | 2.85 | 2.86 |
| Vanilla Flavour (Powder) | 10.00 | 5.01 | 10.00 |
| Sodium Benzoate | 5.00 | 5.01 | 5.00 |
| Methylparaben Sodium | 2.29 | 2.29 | 2.29 |
| Maltitol Powder | 272 | 280 | 272 |
| Titanium Dioxide | 3.89 | 3.90 | 3.89 |
| Water | QS 1 ml | QS 1 ml | QS 1 ml |
| Granulate Composition | mg/g | mg/g | mg/g |
| Omeprazole | 53.73 | 101.98 | 101.98 |
| Sodium Bicarbonate | 914.93 | 868.27 | 868.27 |
| Sodium Alginate | 31.34 | 29.75 | 29.75 |
| Granulate Batch Size (Kg) | 13.400 | 14.120 | 14.120 |
| Granulation Equipment | Yenchen YC-MGB-50/25 Super Mixer/Granulator/50 L Bowl/Yenchen YC -CM-1 Conemill, 0.6 mm screen | | |
| Granulation Solvent | Water | Water | Water |
| Solvent:Solids Ratio (L:Kg) | 0.09 | 0.11 | 0.11 |
| Drying Equipment | Yenchen YC -FBD-15 Fluid Bed Dryer | | |
| Drying Temperature (° C.) | 40 | 40 | 40 |
| Milling Equipment | Yenchen YC-CM-1-Conemill | | |
| Blend Lot No | 17F03 | RD17-017 | 17F06 |
| First mixture Composition | | | |
| Milled Granulate | 881.54 | 887.43 | 887.00 |
| Mannitol | 7.90 | 7.54 | 7.54 |
| Sodium Alginate (Dried) | 110.55 | 105.26 | 105.45 |
| Blend Size (Kg) | 9.100 | 1.368 | 9.540 |
| Blending Equipment | Pharmatech MB 400/50 L Drum | Yenchen V-Mixer 5 L Drum | Pharmatech MB 400/50 L Drum |
| Blending Conditions | 25 rpm/30 mins | 40 rpm/45 mins | 25 rpm/30 mins |
| Caps Lot No | 17F03 | RD 17-017 | 17F06 |
| Cap Filling/Sealing Equipment | MCPI Fine Dosing Opti-feeder/i-DOSiTECNO Table Top Capping Machine | | |
| Target Fill Weight (g) | 3.800 | 3.980 | 3.980 |
| Mean In Process Fill Weight (g) | 3.794 | 3.997 | 3.979 |
| Actual In Process Fill Weight Range | 98.47%-100.79% Target Fill Weight | 100.03%-101.08% Target Fill Weight | 98.94%-101.58% Target Fill Weight |
| Second mixture Batch Size (Kg) | 43.000 | 20.000 | 43.000 |
| Second mixture Composition | | | |
| Sodium Bicarbonate | 35.67 | 35.40 | 35.67 |
| Potassium Bicarbonate | 290.24 | 288.05 | 290.24 |
| Mannitol | 9.71 | 9.65 | 9.71 |
| Sucralose | 8.32 | 8.25 | 8.32 |
| Sodium Alginate (Dried) | 39.83 | 39.65 | 39.83 |
| Xanthan Gum | 5.97 | 5.90 | 5.97 |
| Vanilla Flavour (Powder) | 20.84 | 10.35 | 20.84 |
| Sodium Benzoate | 10.42 | 10.35 | 10.42 |
| Methylparaben Sodium | 4.77 | 4.73 | 4.77 |
| Maltitol Powder | 566.15 | 579.70 | 566.15 |
| Titanium Dioxide | 8.11 | 8.05 | 8.11 |
| Second mixture Sub Lot Batch Size (Kg) | 23.801    23.801 | N/A | 23.801    23.801 |
| Second mixture Sub Lot Manufacturing Equipment | Yenchen YC MGB -50/25 Super Mixer/ Granulator 50 L    Yenchen YC MGB - 50/25 Super Mixer/ Granulator 50 L | N/A | Yenchen YC MGB -50/25 Super Mixer/ Granulator 50 L    Yenchen YC MGB -50/25 Super Mixer/ Granulator 50 L |
| Second mixture Sub Lot Blending Conditions | High speed impellor & chopper for 10 mins pre flavour/ low speed impellor for 3 mins post flavour    High speed impellor & chopper for 10 mins pre flavour/ low speed impellor for 3 mins post flavour | N/A | High speed impellor & chopper for 10 mins pre flavour/ low speed impellor for 3 mins post flavour    High speed impellor & chopper for 10 mins pre flavor/ low speed impellor for 3 mins post flavour |
| Second mixture Manufacturing Equipment | Pharmatech MB 400 (100 L Blender Drum) | Yenchen YC MGB - 50/25 Super Mixer/Granulator 50 L | Pharmatech MB 400 (100 L Blender Drum) |
| Second mixture Blending Conditions | 25 rpm/10 mins | High speed impellor & chopper for 10 mins | 25 rpm/10 mins |

TABLE 1-continued

| Omeprazole Oral Susp'n | Example A | Example B | Example C |
|---|---|---|---|
| Bottle Filling and Capping Equipment | All-Fill Gravimetric Filling Machine/Flexicon Filling System | N/A - Manual | All-Fill Gravimetric Filling Machine/Flexicon Filling System |
| Target Fill Weight (g) | 43.19 | 43.547 | 43.19 |
| Mean In Process Fill Weight (g) | 43.075 | 43.679 | 43.047 |
| Actual In Process Fill Weight Range | 98.16%-101.01% Target Fill Weight | 98.98%-101.04% Target Fill Weight | 98.84%-100.23% Target Fill Weight |

Example 2

Exemplary Formulations of Omeprazole 2 mg/ml and 4 mg/ml Oral Suspensions

TABLE 2

| | Omeprazole Oral Susp'n Strength (mg/ml) | | | | | |
|---|---|---|---|---|---|---|
| | 2 | 2 | 2 | 4 | 4 | 4 |
| Constituted | Omeprazole Oral Suspension Example | | | | | |
| Suspension Composition | Example D mg/ml | Example E mg/ml | Example F mg/ml | Example G mg/ml | Example H mg/ml | Example I mg/ml |
| Omeprazole | 2 | 2 | 2 | 4 | 4 | 4 |
| Sodium Bicarbonate | 51.2 | 51.2 | 51.2 | 51.2 | 51.2 | 51.2 |
| Potassium Bicarbonate | 139 | 139 | 139 | 139 | 139 | 139 |
| Sodium Alginate | 25.0 | 25.0 | 25.0 | 25.0 | 25.0 | 25.0 |
| Mannitol | 5.00 | 5.00 | 5.00 | 5.00 | 5.00 | 5.00 |
| Sucralose | 4.00 | 4.00 | 4.00 | 4.00 | 4.00 | 4.00 |
| Xanthan Gum | 2.86 | 2.86 | 2.86 | 2.86 | 2.86 | 2.86 |
| Mint Flavour (Powder) | 2.50 | 2.50 | 2.50 | 5.00 | 5.00 | 5.00 |
| Vanilla Flavour (Powder) | 10.0 | 10.0 | 10.0 | N/A | N/A | N/A |
| Sodium Benzoate | 5.00 | 5.00 | 5.00 | 5.00 | 5.00 | 5.00 |
| Methyl Paraben Sodium | 2.29 | 2.29 | 2.29 | 2.29 | 2.29 | 2.29 |
| Maltitol Powder | 272 | 272 | 272 | 272 | 272 | 272 |
| Titanium Dioxide | 3.90 | 3.90 | 3.90 | 3.90 | 3.90 | 3.90 |
| Water | qs 1 ml | qs 1 ml | qs 1 ml | qs 1 ml | qs 1 ml | qs 1 ml |
| Buffering Capacity (mEq/ml) | 2 | 2 | 2 | 2 | 2 | 2 |

Example 3

Exemplary Chemical Composition of an Omeprazole Oral Suspension

TABLE 3

| Compound | mg/ml |
|---|---|
| omeprazole | 4 |
| Buffering Agents: | |
| Sodium hydrogen carbonate (sodium bicarbonate) | 51.2 |
| Potassium hydrogen carbonate (potassium bicarbonate) | 139 |
| Granulating agent/internal desiccant/stabilizer/thickener: | |
| Sodium alginate | 25.0 |
| Sweeteners: | |
| Maltitol | 272 |
| Mannitol | 5.00 |
| Sucralose | 4.00 |

TABLE 3-continued

| Compound | mg/ml |
|---|---|
| Viscosity modifier: | |
| Xanthan gum | 2.86 |
| Flavors: | |
| Mint | 5.00 |
| Opacifier: | |
| Titanium oxide | 3.90 |
| Preservative system: | |
| Sodium benzoate | 5.00 |
| Sodium methylparaben | 2.29 |
| Buffering capacity | 2 mEq/ml |

Example 4

This example demonstrates the benefit of the storage-stable omeprazole powder systems of the disclosure on the stability of constituted omeprazole oral suspensions according to the present disclosure.

Omeprazole 2 mg/ml oral suspensions of Example J, Example K, and Example L were prepared having identical constituted suspension compositions, but they included the following differences:

Example J is an aluminium (Alu) foil packaged two chamber dosage form according to the present disclosure comprising a cap containing a first powder mixture fastened on a bottle containing a second powder mixture;

Example K is a comparative example of an Alu foil packaged two chamber dosage form comprising a cap containing a first powder mixture fastened on a bottle containing a second powder mixture which had been constituted with water; and Example L is a comparative example of an Alu foil packaged single chamber dosage form comprising a capped bottle containing a powder mixture of a first powder mixture and a second powder mixture.

A description of the manufacturing, packaging and constitution details for the prepared omeprazole 2 mg/ml suspensions of Examples J, K, and L is provided below:

| Drying of Sodium Alginate (Batch Size: 3.600 Kg) |
| --- |
| 1. Sodium alginate was dried in a VD53 Binder Vacuum Drying Oven (i) under a vacuum of approximately 600 mbar and a temperature setting of approximately 85° C. until a loss on drying specification of NMT 3% was met and then (ii) under a vacuum of <100 mbar and a temperature setting of approximately 85° C. until a loss on drying specification of NMT 2% was met. |
| Manufacture of Omeprazole Granulate (Batch Size: 13.400 Kg) |
| 2. Sodium hydrogen carbonate, micronised omeprazole and sodium alginate were added, via a 2 mm screen, to the Yenchen Super Mixer/Granulator YC-MGB-50/25 (50 L bowl), and mixed for approximately 15 minutes at high impellor speed and high chopper speed. |
| 3. 1250 ml purified water was added to the sodium hydrogen carbonate, micronised omeprazole and sodium alginate dry mixture in the Yenchen Super Mixer/Granulator YC-MGB-50/25 over approximately 5 minutes, while mixing at low impellor speed and high chopper speed. Mixing was continued for approximately 1 further minute at low impellor speed and high chopper speed after which the mixture was mixed for approximately 1 minute at high impellor speed and high chopper speed. |
| 4. The wet granulate was screened through a 2 mm screen using a Yenchen YC-CM-1 Cone Mill at approximately 600 rpm. |
| 5. The screened wet granulate was loaded into a Yenchen YC-FBD-15 Fluid Bed Dryer and the granules were dried at a temperature setting of approximately 40° C. until the loss of drying specification of NMT 1.5% was met. |
| 6. The resulting dry granulate was milled initially through a 0.8 mm screen, and then through a 0.6 mm screen, using a Yenchen YC-CM-1 Cone Mill at approximately 450 rpm. |
| Manufacture of First Powder Mixture (Batch Size: 9.100 Kg) |
| 7. The milled dry granulate, mannitol (via a 0.8 mm screen) and dried sodium alginate (via a 0.8 mm screen) were loaded into a Pharmatech Multiblend Blender MB 400 (50 L drum) and blended for approximately 30 minutes at approximately 25 rpm. |
| PICS Cap Manufacture (Batch Size: 2394 caps) |
| 8. The first powder mixture was filled into polypropylene PICS Caps to a target fill weight of 3.80 g on a MCPI Fine Dosing Optifeeder. The head space above the powder fill in the PICS Caps was partially evacuated under vacuum and then flushed with nitrogen before sealing the PICS Caps with the seal disks using the i-DOSiTECHNO Table Top Capping Machine. |
| Second Powder Mixture Manufacture [23.929 Kg] |
| 9. Potassium hydrogen carbonate was milled initially through a 2 mm screen, and then through a 0.6 mm screen, at approximately 450 rpm using a Yenchen YC-CM-1 Cone Mill. |
| 10. Sodium methyl parahydroxybenzoate was screened through a 0.8 mm mesh hand screen. |
| 11. Maltitol, milled potassium hydrogen carbonate, dried sodium alginate, sodium hydrogen carbonate, sodium benzoate, mannitol, sucralose, titanium dioxide, xanthan gum and screened sodium methyl parahydroxybenzoate were screened through a 2 mm mesh hand screen into a Yenchen Super Mixer/Granulator YC-MGB-50/25 (50 L Bowl) and blended for approximately 10 minutes at high impellor speed and high chopper speed. The mint and vanilla flavours, via a 2 mm mesh hand screen, were added to the resulting mixture in the Yenchen Super Mixer/Granulator YC-MGB-50/25 and blended for approximately 3 minutes at low impellor speed. |
| Bottle Filling and Capping [Batch Size: 200 Bottles] |
| 12. The final second powder mixture was filled into 150 ml amber PET bottles to a target fill weight of 43.40 g using an All Fill Series 10 Gravimetric Filling Machine and the bottles were capped with the first powder mixture filled PICS Caps using a Flexicon FF30 Table Top Capping equipment. |
| Further Processing including Packaging |
| 13. Example J-Alu Foil Packaged Two Chamber Dosage Form Comprising PICS Cap Containing First Powder Mixture Fastened on Bottle Containing Second Powder Mixture. |

| Drying of Sodium Alginate (Batch Size: 3.600 Kg) |
| --- |
| The filled and capped bottles from Step 12 were packaged by placing the bottle in an Alu Foil Pouch and sealing the open end of the Alu Foil Pouch using a Hawo hpl WSZ Hand Sealer (temperature setting 150° C., holding time one to two seconds). Example K - Alu Foil Packaged Two Chamber Dosage Form Comprising PICS Cap Containing First Powder Mixture Fastened on Bottle Containing Second Powder Mixture which had been Constituted with Water. The second powder mixture contents of the bottle for the filled and capped bottles from Step 12 was constituted as follows: The powder was loosened by shaking/agitating the bottle vigorously for 20 seconds. The base of the bottle was tapped three times on a hard horizontal surface. The first powder mixture filled PICS Cap was removed from the bottle. 64 ml of water was added to the second powder mixture content of the bottle. The first powder mixture filled PICS Cap was securely refastened onto the bottle. The bottle was shaken vigorously for 30 seconds. The resulting capped bottles were packaged by placing the capped bottle in an Alu Foil Pouch and sealing the open end of the Alu Foil Pouch using a Hawo hpl WSZ Hand Sealer (temperature setting 150° C., holding time one to two seconds). The alu foil packaged bottles were loaded upright in a cardboard box. Example L - Alu Foil Packaged Single Chamber Dosage Form Comprising a Capped Bottle Containing a Powder Mixture of First Powder Mixture and Second Powder Mixture The contents of the PICS Cap and the contents of the bottle for the filled and capped bottles from Step 12 were mixed as follows: The powder was loosened by shaking/agitating the bottle for 10 seconds. The powder in the red PICS cap was released into the bottle by twisting the red cap anti-clockwise until the seal was broken. The red cap was twisted back to the original position, securely fastening the red cap onto the bottle. While holding the bottle upright, the powder was swirled for ten seconds. The bottle was shaken vigorously for a further 10 seconds. The base of the bottle was tapped three times on a hard horizontal surface. The resulting capped and bottled mixture was packaged by placing the bottle in an Alu Foil Pouch and sealing the open end of the Alu Foil Pouch using a Hawo hpl WSZ Hand Sealer (temperature setting 150° C. , holding time one to two seconds). |
| Followed Constitution Instructions |
| Example J Shake the bottle for 10 seconds to loosen the powder. Twist the red cap anti-clockwise until the seal is broken to release the powder in the red cap into the bottle. Twist the red cap back to the original position, securely fastening the red cap onto the bottle. Shake the bottle vigorously for ten seconds. Tap the base of the bottle three times on a hard horizontal surface. Remove the red cap from the bottle. Add 64 mL of water by using a suitable measuring device. Securely fasten the red cap onto the bottle and shake vigorously for 30 seconds. Remove the red cap and red ring and throw away. Insert the Bottle Adaptor and replace the red cap with the grey plastic screw-cap. Leave for fifteen minutes. Shake for 20 seconds prior to each use. Example K Shake the bottle for 10 seconds to loosen the powder. Twist the red cap anti-clockwise until the seal is broken to release the powder in the red cap into the bottle. Twist the red cap back to the original position, securely fastening the red cap onto the bottle. Tap the base of the bottle three times on a hard horizontal surface. Securely fasten the red cap onto the bottle and shake vigorously for 30 seconds. Remove the red cap and red ring and throw away. Insert the Bottle Adaptor and replace the red cap with the grey plastic screw-cap. Leave for fifteen minutes. Shake for 20 seconds prior to each use. Example L Shake the bottle for 10 seconds to loosen the powder. Tap the base of the bottle three times on a hard horizontal surface. Remove the red cap from the bottle. Add 64 mL of water by using a suitable measuring device. Securely fasten the red cap onto the bottle and shake vigorously for 30 seconds. Remove the red cap and red ring and throw away. Insert the Bottle Adaptor and replace the red cap with the grey plastic screw-cap. Leave for fifteen minutes. Shake for 20 seconds prior to each use. |

A summary of the formulation and characterization details of the omeprazole 2 mg/ml oral suspensions of Example J, Example K, and Example L is provided in Table 4.

TABLE 4

| OMEPRAZOLE 2 MG/ML SUSPENSIONS | Example J | Example K | Example L |
| --- | --- | --- | --- |
| DESCRIPTION OF DOSAGE FORM BEFORE CONSTITUTION OF FINISHED PRODUCT | Alu Foil Packaged Two Chamber Dosage Form Comprising Cap Containing First Powder | Alu Foil Packaged Two Chamber Dosage Form Comprising Cap Containing First Powder | Alu Foil Packaged Single Chamber Dosage Form Comprising a Capped |

TABLE 4-continued

| OMEPRAZOLE 2 MG/ML SUSPENSIONS | Example J | Example K | Example L |
|---|---|---|---|
| | Mixture Fastened on Bottle Containing Second Powder Mixture | Mixture Fastened on Bottle Containing Second Powder Mixture which had been Constituted with Water | Bottle Containing a Powder Mixture of First Powder Mixture and Second Powder Mixture |
| FIRST POWDER MIXTURE COMPONENT | | | |
| Average LOD of Omeprazole Granulate | 0.52% | 0.52% | 0.52% |
| Omeprazole Granulate Composition | mg/g | mg/g | mg/g |
| Omeprazole | 53.73 | 53.73 | 53.73 |
| Sodium Bicarbonate | 914.93 | 914.93 | 914.93 |
| Sodium Alginate | 31.34 | 31.34 | 31.34 |
| Average LOD of Dried Alginate | 1.05% | 1.05% | 1.05% |
| First Powder Mixture Composition | | | |
| Milled Omeprazole Granulate | 881.58 | 881.58 | 881.58 |
| Mannitol | 7.90 | 7.90 | 7.90 |
| Sodium Alginate (Dried) | 110.52 | 110.52 | 110.52 |
| Average LOD of First Powder Mixture | 0.70% | 0.70% | 0.70% |
| SECOND POWDER MIXTURE COMPONENT | | | |
| Average LOD of Dried Alginate | 0.79% | 0.79% | 0.79% |
| Second Powder Mixture Composition | | | |
| | (before addition of 64 ml water) | | |
| Sodium Bicarbonate | 35.46 | 35.46 | 35.46 |
| Potassium Bicarbonate | 288.72 | 288.72 | 288.72 |
| Mannitol | 9.67 | 9.67 | 9.67 |
| Sucralose | 8.30 | 8.30 | 8.30 |
| Sodium Alginate (Dried) | 39.60 | 39.60 | 39.60 |
| Xanthan Gum | 5.93 | 5.93 | 5.93 |
| Mint Flavour | 5.19 | 5.19 | 5.19 |
| Vanilla Flavour | 20.74 | 20.74 | 20.74 |
| Sodium Benzoate | 10.37 | 10.37 | 10.37 |
| Methylparaben Sodium | 4.74 | 4.74 | 4.74 |
| Maltitol Powder | 563.20 | 563.20 | 563.20 |
| Titanium Dioxide | 8.08 | 8.08 | 8.08 |
| Average LOD of Second Powder Mixture | 0.6% | 0.6% | 0.6% |
| CONSTITUTED FINISHED PRODUCT | | | |
| Constituted Suspension Composition | mg/ml | mg/ml | mg/ml |
| Omeprazole | 2 | 2 | 2 |
| Sodium Bicarbonate | 51.2 | 51.2 | 51.2 |
| Potassium Bicarbonate | 139 | 139 | 139 |
| Sodium Alginate | 1.17 | 1.17 | 1.17 |
| Mannitol | 5.00 | 5.00 | 5.00 |
| Sucralose | 4.00 | 4.00 | 4.00 |
| Sodium Alginate (Dried) | 23.8 | 23.8 | 23.8 |
| Xanthan Gum | 2.86 | 2.86 | 2.86 |
| Mint Flavour | 2.50 | 2.50 | 2.50 |
| Vanilla Flavour | 10.00 | 10.00 | 10.00 |
| Sodium Benzoate | 5.00 | 5.00 | 5.00 |
| Methylparaben Sodium | 2.29 | 2.29 | 2.29 |
| Maltitol Powder | 272 | 272 | 272 |
| Titanium Dioxide | 3.90 | 3.90 | 3.90 |
| Water | qs 1 ml | qs 1 ml | qs 1 ml |
| Sodium Content of Finished Product | 86 mg/5 ml | 86 mg/5 ml | 86 mg/5 ml |
| Sodium:Potassium in Finished Product | 1:3.2 | 1:3.2 | 1:3.2 |
| Sodium Bicarbonate:Potassium Bicarbonate in Finished Product | 1:2.7 | 1:2.7 | 1:2.7 |
| Buffering Capacity of Finished Product | 2 mEq/ml | 2 mEq/ml | 2 mEq/ml |

A summary of the results of the stability study on the omeprazole 2 mg/ml oral suspensions of Example J, Example K, and Example L is provided in Table 5.

TABLE 5

| OMEPRAZOLE 2 MG/ML SUSPENSION | Example J | Example K | Example L |
|---|---|---|---|
| DESCRIPTION OF DOSAGE FORM BEFORE CONSTITUTION OF FINISHED PRODUCT | Alu Foil Packaged Two Chamber Dosage Form Comprising Cap Containing First Powder Mixture Fastened on | Alu Foil Packaged Two Chamber Dosage Form Comprising Cap Containing First Powder Mixture Fastened on | Alu Foil Packaged Single Chamber Dosage Form Comprising a Capped Bottle Containing a |

TABLE 5-continued

| OMEPRAZOLE 2 MG/ML SUSPENSION | Example J | Example K | Example L |
|---|---|---|---|
| | Bottle Containing Second Powder Mixture | Bottle Containing Second Powder Mixture which had been Constituted with Water | Powder Mixture of First Powder Mixture and Second Powder Mixture |
| STABILITY | | | |
| Stability Storage Conditions | 40° C./75% RH for 3 months (Alu Foil Packaged Product) then 2 months at 2° C.-8° C. (Constituted Finished Product) | 40° C./75% RH for 3 months (Alu Foil Packaged Product) then 2 months at 2° C.-8° C. (Constituted Finished Product) | 40° C./75% RH for 3 months (Alu Foil Packaged Product) then 2 months at 2° C.-8° C. (Constituted Finished Product) |
| Constituted Product on Day of Constitution | | | |
| Total Impurities | 0.11% | 1.49% | 7.59% |
| Sodium Benzoate Content | 100.5% | 98.3% | Not Tested |
| Sodium Methyl Parahydroxybenzoate Content | 95.9% | 10.1% | Not Tested |
| pH | 8.1 | 8.3 | 8.1 |
| Buffer Capacity | 2.0 mEq/ml | 2.0 mEq/ml | 2.1 mEq/ml |
| Constituted Product after 28 days at 2°-8° C. | | | |
| Total Impurities | 0.23% | 2.19% | 6.79% |
| Sodium Benzoate Content | 98% | 96.6% | Not Tested |
| Sodium Methyl Parahydroxybenzoate Content | 94% | 10.4% | Not Tested |
| pH | 8.3 | 8.5 | 8.3 |
| Buffer Capacity | 2.0 mEq/ml | 2.0 mEq/ml | 2.1 mEq/ml |
| Constituted Product after 56 days at 2°-8° C. | | | |
| Total Impurities | 0.33% | 4.41% | 11.02% |
| Sodium Benzoate Content | 93.4% | 95.8% | Not Tested |
| Sodium Methyl Parahydroxybenzoate Content | 86.1% | 10.3% | Not Tested |
| pH | 8.1 | 8.3 | 8.3 |
| Buffer Capacity | 2.1 mEq/ml | 2.0 mEq/ml | 2.0 mEq/ml |

Example 5

An Exemplary Chemical Composition of an Omeprazole Oral Suspension Prepared Using Micronized Omeprazole A description of the manufacturing, packaging and constitution details for the prepared omeprazole 4 mg/ml suspension of Example M is provided below:

| Drying of Sodium Alginate (Batch Size: 3.600 Kg) |
|---|
| 1. Sodium alginate was dried in a VD53 Binder Vacuum Drying Oven (i) under a vacuum of approximately 600 mbar and a temperature setting of approximately 85° C. until a loss on drying specification of NMT 3% was met and then (ii) under a vacuum of <100 mbar and a temperature setting of approximately 85° C. until a loss on drying specification of NMT 2% was met |

| Manufacture of Omeprazole Granulate (Batch Size: 14.120 Kg) |
|---|
| 2. Sodium hydrogen carbonate, micronised omeprazole and sodium alginate were added, via a 2 mm screen, to the Yenchen Super Mixer/Granulator YC-MGB-50/25 (50 L bowl), and mixed for approximately 15 minutes at high impellor speed and high chopper speed. |
| 3. 1550 ml purified water was added to the sodium hydrogen carbonate, micronised omeprazole and sodium alginate dry mixture in the Yenchen Super Mixer/Granulator YC-MGB-50/25 over approximately 5 minutes, while mixing at low impellor speed and high chopper speed. The mixture was mixed for approximately 1 further minute at low impellor speed and high chopper speed after which it was mixed for approximately 1 minute at high impellor speed and high chopper speed. |
| 4. The wet granulate was screened through a 2 mm screen using a Yenchen YC-CM-1 Cone Mill at approximately 600 rpm. |
| 5. The screened wet granulate was loaded into a Yenchen YC-FBD-15 Fluid Bed Dryer and the granules were dried at a temperature setting of approximately 40° C. until the loss of drying specification of NMT 1.5% was met. |

-continued

| |
|---|
| 6. The resulting dry granulate was milled initially through a 0.8 mm screen, and then through a 0.6 mm screen, using a Yenchen YC-CM-1 Cone Mill at approximately 450 rpm. |

Manufacture of First Powder Mixture (Batch Size: 9.540 Kg)

| |
|---|
| 7. The milled dry granulate, mannitol (via a 0.8 mm screen) and dried sodium alginate (via a 0.8 mm screen) were loaded into a Pharmatech Multiblend Blender MB 400 (50 L drum) and blended for approximately 30 minutes at approximately 25 rpm. |

PICS Cap Manufacture (Batch Size: 2396 caps)

| |
|---|
| 8. The first powder mixture was filled into polypropylene PICS Caps to a target fill weight of 3.98 g on a MCPI Fine Dosing Optifeeder. The head space above the powder fill in the PICS Caps was partially evacuated under vacuum and then flushed with nitrogen before sealing the PICS Caps with the seal disks using an i-DOSiTECHNO Table Top Capping Machine. |

Second Powder Mixture Sub Lot Manufacture [23.500 Kg]

| |
|---|
| 9. Potassium hydrogen carbonate was milled initially through a 2 mm screen, and then through a 0.6 mm screen, at approximately 450 rpm using a Yenchen YC-CM-1 Cone Mill. |
| 10. Sodium methyl parahydroxybenzoate was screened through a 0.8 mm mesh hand screen. |
| 11. Maltitol, milled potassium hydrogen carbonate, dried sodium alginate, sodium hydrogen carbonate, sodium benzoate, mannitol, sucralose, titanium dioxide, xanthan gum and screened sodium methyl parahydroxybenzoate were screened through a 2 mm mesh hand screen into a Yenchen Super Mixer/Granulator YC-MGB-50/25 (50 L Bowl) and blended for approximately 10 minutes at high impellor speed and high chopper speed. The mint flavour was added via a 2 mm mesh hand screen, to the resulting mixture in the Yenchen Super Mixer/Granulator YC-MGB-50/25 and blended for approximately 3 minutes at low impellor speed. |
| 12. Steps 9, 10 and 11 were repeated for a further second powder mixture sublot. |

Final Second Powder Mixture Manufacture (45 Kg)

| |
|---|
| 13. The two second powder mixture sub lots were added into a Pharmatech Multiblend Blender MB 400 (100 L drum) and blended for approximately 10 minutes at approximately 25 rpm |

Bottle Filling and Capping [Batch Size: 1052 Bottles]

| |
|---|
| 14. The final second powder mixture was filled into 150 ml amber PET bottles to a target fill weight of 42.75 g using an All Fill Series 10 Gravimetric Filling Machine and the bottles were capped with the first powder mixture filled PICS Caps using a Flexicon FF30 Table Top Capping equipment. |

Further Processing including Packaging

| |
|---|
| 15. The filled and capped bottles from Step 14 were packaged by placing the bottle in an Alu Foil Pouch and sealing the open end of the Alu Foil Pouch using a Hawo hpl WSZ Hand Sealer (temperature setting 150° C., holding time one to two seconds). |

Followed Constitution Instructions

Example M
Shake the bottle for 10 seconds to loosen the powder. Twist the red cap anti-clockwise until the seal is broken to release the powder in the red cap into the bottle. Twist the red cap back to the original position, securely fastening the red cap onto the bottle. Shake the bottle vigorously for ten seconds. Tap the base of the bottle three times on a hard horizontal surface. Remove the red cap from the bottle. Add 64 mL of water by using a suitable measuring device. Securely fasten the red cap onto the bottle and shake vigorously for 30 seconds. Remove the red cap and red ring and throw away. Insert the Bottle Adaptor and replace the red cap with the grey plastic screw-cap. Leave for fifteen minutes. Shake for 20 seconds prior to each use.

A summary of the formulation and characterization details of the omeprazole 4 mg/ml oral suspension of Example M is provided in Table 6.

TABLE 6

| OMEPRAZOLE 4 MG/ML SUSPENSION | Example M |
|---|---|
| DESCRIPTION OF DOSAGE FORM BEFORE CONSTITUTION OF FINISHED PRODUCT | Alu Foil Packaged Two Chamber Dosage Form Comprising Cap Containing First Powder Mixture Fastened on Bottle Containing Second Powder Mixture |
| FIRST POWDER MIXTURE COMPONENT | |
| Omeprazole Granulate Composition | mg/g |
| Omeprazole | 101.98 |
| Sodium Bicarbonate | 868.27 |
| Sodium Alginate | 29.75 |
| Average LOD of Omeprazole Granulate | 0.62% |
| Average LOD of Dried Alginate | 1.30% |
| First Powder Mixture Composition | |
| Milled Omeprazole Granulate | 886.96 |
| Mannitol | 7.54 |
| Sodium Alginate (Dried) | 105.50 |
| Average LOD of First Powder Mixture | 0.83% |
| SECOND POWDER MIXTURE COMPONENT | |
| Average LOD of Dried Alginate | 1.30% |
| Second Powder Mixture Composition | |
| Sodium Bicarbonate | 36.03 |
| Potassium Bicarbonate | 293.29 |
| Mannitol | 9.82 |
| Sucralose | 8.42 |
| Sodium Alginate (Dried) | 40.36 |
| Xanthan Gum | 6.03 |
| Mint Flavour | 10.52 |
| Sodium Benzoate | 10.52 |
| Methylparaben Sodium | 4.82 |
| Maltitol Powder | 571.99 |
| Titanium Dioxide | 8.20 |
| Average LOD of Final Second Powder Mixture | 0.50% |
| CONSTITUTED FINISHED PRODUCT | |
| Constituted Suspension Composition | mg/ml |
| Omeprazole | 4 |
| Sodium Bicarbonate | 51.2 |
| Potassium Bicarbonate | 139 |
| Sodium Alginate | 1.17 |
| Mannitol | 5.00 |
| Sucralose | 4.00 |
| Sodium Alginate (Dried) | 23.8 |
| Xanthan Gum | 2.86 |
| Mint Flavour | 5.00 |
| Sodium Benzoate | 5.00 |
| Methylparaben Sodium | 2.29 |
| Maltitol Powder | 272 |
| Titanium Dioxide | 3.90 |
| Water | qs 1 ml |
| Sodium Content of Finished Product | 86 mg/5 ml |
| Sodium:Potassium in Finished Product | 1:3.2 |
| Sodium Bicarbonate:Potassium Bicarbonate in Finished Product | 1:2.7 |
| Buffering Capacity | 2 mEq/ml |

A summary of the results of a stability study on the omeprazole 4 mg/ml oral suspension of Example M is provided in Table 7.

TABLE 7

| OMEPRAZOLE 4 MG/ML SUSPENSION | Example M | | | | |
|---|---|---|---|---|---|
| DESCRIPTION OF DOSAGE FORM BEFORE CONSTITUTION OF FINISHED PRODUCT | Alu Foil Packaged Two Chamber Dosage Form Comprising Cap Containing First Powder Mixture Fastened on Bottle Containing Second Powder Mixture | | | | |
| STABILITY | | | | | |
| | 25° C./60% RH for 24 months (Alu Foil Packaged Product) | | | | |
| Stability Storage Conditions | T = 0 | T = 6 months | T = 12 months | T = 18 month | T = 24 months |
| Omeprazole Content | 97% | 102% | 99% | 100% | 99% |
| LOD (Contents of PICS Cap Chamber) | 0.8% | 0.9% | 0.9% | 0.9% | 0.7% |
| LOD (Contents of Bottle Chamber) | 0.5% | 0.8% | 0.7% | 0.7% | 0.7% |
| Total Impurities | <0.05% | 0.10% | 0.10% | 0.10% | 0.05% |
| Sodium Benzoate Content | 98% | 100% | 98% | 99% | 99% |
| Sodium Methyl Parahydroxybenzoate Content | 100% | 99% | 99% | 101% | 100% |
| pH | 8.1 | Not Tested | 8.0 | 8.1 | 8.1 |

Example 6

Exemplary Chemical Compositions of Omeprazole Oral Suspensions Prepared Using a Mixture of Micronized and Non-Micronized Omeprazole A description of the manufacturing, packaging and constitution details for the prepared omeprazole 4 mg/ml suspensions of Examples N and O is provided below:

Drying of Sodium Alginate (Batch Size: 9.000 Kg)

1. Dry sodium alginate was prepared in a Yenchen YC-FBD-15 Fluid Bed Dryer at a temperature setting of approximately 70° C. until the loss of drying specification of no more than (NMT) 2.0% was met.

Manufacture of Omeprazole Granulate (Batch Size: 14.120 Kg)

2. Sodium hydrogen carbonate, micronised omeprazole, sieved (non-micronised) omeprazole and sodium alginate were added via a 2 mm screen, to a Yenchen Super Mixer/Granulator YC-MGB-50/25 (50 L bowl), and mixed for approximately 15 minutes at high impellor speed and high chopper speed.
3. 1500 ml of purified water was added to the sodium hydrogen carbonate, micronised omeprazole, sieved (non-micronised) omeprazole and sodium alginate dry mixture in the Yenchen Super Mixer/Granulator YC-MGB-50/25 over approximately 5 minutes, while mixing at low impellor speed and high chopper speed. Mixing was continued for approximately 1 further minute at low impellor speed and high chopper speed after which the mixture was mixed for approximately 1 minute at high impellor speed and high chopper speed.
4. The wet granulate was screened through a 2 mm screen using a Yenchen YC-CM-1 Cone Mill at approximately 600 rpm.
5. The screened wet granulate was loaded into a Yenchen YC-FBD-15 Fluid Bed Dryer and the granules were dried at a temperature setting of approximately 40° C. until the loss of drying specification of NMT 1.5% was met.
6. The resulting dry granulate was milled through a 0.6 mm screen, using a Yenchen YC-CM-1 Cone Mill at approximately 450 rpm.

Manufacture of First Powder Mixture (Batch Size: 10.903 Kg)

7. The milled dry granulate, mannitol (via a 0.8 mm screen) and dried sodium alginate (via a 0.8 mm screen) were loaded into a Pharmatech Multiblend Blender MB 400 (50 L drum) and blended for approximately 30 minutes at approximately 25 rpm.

PICS Cap Manufacture (Batch Size: 2739 caps)

8. The first powder mixture was filled into polypropylene PICS Caps to a target fill weight of 3.98 g on a MCPI Fine Dosing Optifeeder. The head space above the powder fill in the PICS Caps was partially evacuated under vacuum and then flushed with nitrogen before sealing the PICS Caps with the seal disks using an i-DOSiTECHNO Table Top Capping Machine.

Second Powder Mixture Sub Lot Manufacture [23.500 Kg]

9. Potassium hydrogen carbonate was milled initially through a 2 mm screen, and then through a 0.6 mm screen, at approximately 450 rpm using a Yenchen YC-CM-1 Cone Mill.

| Drying of Sodium Alginate (Batch Size: 9.000 Kg) |
|---|
| 10. Sodium methyl parahydroxybenzoate was screened through a 0.8 mm mesh hand screen.
11. Maltitol, milled potassium hydrogen carbonate, dried sodium alginate, sodium hydrogen carbonate, sodium benzoate, mannitol, sucralose, titanium dioxide, xanthan gum and screened sodium methyl parahydroxybenzoate were screened through a 2 mm mesh hand screen into a Yenchen Super Mixer/Granulator YC-MGB-50/25 (50 L Bowl) and blended for approximately 10 minutes at high impellor speed and high chopper speed. The mint flavour was added, via a 2 mm mesh hand screen, to the resulting mixture in the Yenchen Super Mixer/Granulator YC-MGB-50/25 and blended for approximately 3 minutes at low impellor speed.
12. Steps 9, 10 and 11 were repeated for a further four second powder mixture sublots. |
| Final Second Powder Mixture Manufacture (112.500 Kg) |
| 13. The five second powder mixture sub lots were added into the Pharmatech Multiblend Blender MB 400 (200 L drum) and blended for approximately 10 minutes at approximately 25 rpm. |
| Bottle Filling and Capping [Batch Size: 1000 Bottles] |
| 14. The final second powder mixture was filled into 150 ml amber PET bottles to a target fill weight of 42.75 g using an All Fill Series 10 Gravimetric Filling Machine and the bottles were capped with the first powder mixture filled PICS Caps using a Flexicon FF30 Table Top Capping equipment. |
| Further Processing including Packaging |
| 15. The filled and capped bottles from Step 14 were packaged by placing the bottle in an Alu Foil Pouch and sealing the open end of the Alu Foil Pouch using a Hawo hpl WSZ Hand Sealer (temperature setting 150° C., holding time one to two seconds). |
| Followed Constitution Instructions |
| Example N and Example O
Shake the bottle for 10 seconds to loosen the powder. Twist the red cap anti-clockwise until the seal is broken to release the powder in the red cap into the bottle. Twist the red cap back to the original position, securely fastening the red cap onto the bottle. Shake the bottle vigorously for ten seconds. Tap the base of the bottle three times on a hard horizontal surface. Remove the red cap from the bottle. Add 64 mL of water by using a suitable measuring device. Securely fasten the red cap onto the bottle and shake vigorously for 30 seconds. Remove the red cap and red ring and throw away. Insert the Bottle Adaptor and replace the red cap with the grey plastic screw-cap. Leave for fifteen minutes. Shake for 20 seconds prior to each use. |

A summary of formulation and characterization details of the omeprazole 4 mg/ml oral suspensions of Examples N and O is provided in Table 8.

TABLE 8

| OMEPRAZOLE 4 MG/ML SUSPENSION | Example N | Example O |
|---|---|---|
| DESCRIPTION OF DOSAGE FORM BEFORE CONSTITUTION OF FINISHED PRODUCT | Alu Foil Packaged Two Chamber Dosage Form Comprising Cap Containing First Powder Mixture Fastened on Bottle Containing Second Powder Mixture | Alu Foil Packaged Two Chamber Dosage Form Comprising Cap Containing First Powder Mixture Fastened on Bottle Containing Second Powder Mixture |
| FIRST POWDER MIXTURE COMPONENT | | |
| Omeprazole Granulate Composition | mg/g | mg/g |
| Omeprazole (micronized) | 30.59 | 61.19 |
| Omeprazole (sieved) | 71.39 | 40.79 |
| Sodium Bicarbonate | 868.27 | 868.27 |
| Sodium Alginate | 29.75 | 29.75 |
| Average LOD of Omeprazole Granulate | 0.28% | 0.38% |
| Average LOD of Dried Alginate | 0.79% | 0.79% |
| First Powder Mixture Composition | | |
| Milled Omeprazole Granulate | 886.96 | 886.96 |
| Mannitol | 7.54 | 7.54 |

TABLE 8-continued

| OMEPRAZOLE 4 MG/ML SUSPENSION | Example N | Example O |
|---|---|---|
| Sodium Alginate (Dried) | 105.50 | 105.50 |
| Average LOD of First Powder Mixture | 0.69% | 0.59% |
| SECOND POWDER MIXTURE COMPONENT | | |
| Average LOD of Dried Alginate | 0.79% | 0.79% |
| Second Powder Mixture Composition | | |
| Sodium Bicarbonate | 36.03 | 36.03 |
| Potassium Bicarbonate | 293.29 | 293.29 |
| Mannitol | 9.82 | 9.82 |
| Sucralose | 8.42 | 8.42 |
| Sodium Alginate (Dried) | 40.36 | 40.36 |
| Xanthan Gum | 6.03 | 6.03 |
| Mint Flavour | 10.52 | 10.52 |
| Sodium Benzoate | 10.52 | 10.52 |
| Methylparaben Sodium | 4.82 | 4.82 |
| Maltitol Powder | 571.99 | 571.99 |
| Titanium Dioxide | 8.20 | 8.20 |
| Average LOD of Final Second Powder Mixture | 0.54% | 0.54% |
| CONSTITUTED FINISHED PRODUCT | | |
| Constituted Suspension Composition | mg/ml | mg/ml |
| Omeprazole | 4 | 4 |
| Sodium Bicarbonate | (30:70 micronised:sieved) 51.2 | (60:40 micronised:sieved) 51.2 |
| Potassium Bicarbonate | 139 | 139 |
| Sodium Alginate | 1.17 | 1.17 |
| Mannitol | 5.00 | 5.00 |
| Sucralose | 4.00 | 4.00 |
| Sodium Alginate (Dried) | 23.8 | 23.8 |
| Xanthan Gum | 2.86 | 2.86 |
| Mint Flavour | 5.00 | 5.00 |
| Sodium Benzoate | 5.00 | 5.00 |
| Methylparaben Sodium | 2.29 | 2.29 |
| Maltitol Powder | 272 | 272 |
| Titanium Dioxide | 3.90 | 3.90 |
| Water | qs 1 ml | qs 1 ml |
| Sodium Content of Finished Product | 86 mg/5 ml | 86 mg/5 ml |
| Sodium:Potassium in Finished Product | 1:3.2 | 1:3.2 |
| Sodium Bicarbonate:Potassium Bicarbonate in Finished Product | 1:2.7 | 1:2.7 |
| Omeprazole Content | 99% label claim | 97% label claim |
| LOD (Contents of PICS Cap Chamber) | 0.6% | 0.5% |
| LOD (Contents of Bottle Chamber) | 0.6% | 0.6% |
| Total Impurities | <0.05% | <0.05% |
| Sodium Benzoate Content | 99% | 97% |
| Sodium Methyl Parahydroxybenzoate Content | 99% | 97% |
| pH | 8.2 | 8.1 |
| Buffer Capacity | 2.1 mEq/ml | 2.1 mEq/ml |

Having now fully described this disclosure, it will be understood by those of ordinary skill in the art that the same can be performed within a wide and equivalent range of conditions, formulations, and other parameters without affecting the scope of the invention or any embodiment thereof.

Other embodiments described herein will be apparent to those skilled in the art from consideration of the specification and practice of the invention disclosed herein. It is intended that the specification be considered exemplary only, with a true scope and spirit of the invention being indicated by the following claims.

All patents, patent applications, and publications cited herein are fully incorporated by reference herein in their entirety.

What is claimed is:

1. A storage-stable omeprazole powder system, the system comprising (i) a first powder mixture comprising (a) a therapeutically effective amount of omeprazole, or a pharmaceutically acceptable salt thereof, (b) sodium alginate, and (c) a first buffering agent; and (ii) a second powder mixture comprising sodium alginate and a second buffering agent, wherein the first powder mixture and the second powder mixture are stored separately from each other and are mixed together on or just before constitution with water, and wherein the system contains sodium and potassium at a ratio of from about 1:2.6 to about 1:3.4 by weight.

2. The storage-stable omeprazole powder system of claim 1, wherein the omeprazole or the pharmaceutically acceptable salt thereof is micronized.

3. The storage-stable omeprazole powder system of claim 1, wherein the omeprazole or the pharmaceutically acceptable salt thereof is a mixture of micronized and non-micronized omeprazole, or the pharmaceutically acceptable salt thereof.

4. The storage-stable omeprazole powder system of claim 1, wherein the first and second buffering agents are each independently selected from the group consisting of sodium bicarbonate, potassium bicarbonate, and a mixture thereof.

5. The storage-stable omeprazole powder system of claim 1, wherein the storage-stable omeprazole powder system is provided in a drug delivery device suitable for multi-dose administration of omeprazole.

6. The storage-stable omeprazole powder system of claim 5, wherein the storage-stable omeprazole powder system is provided in a container body comprising a cap, wherein (i) the container body contains the second powder mixture and has a container opening formed in an upper end thereof; (ii) the cap comprises a cylindrical accommodation portion comprising the first powder mixture and a cap portion sealing an upper end of the accommodation portion, and wherein (iii) the cap is mounted in the container opening of the container body, wherein when the cap is twisted, the first powder mixture is released into the container body.

7. The storage-stable omeprazole powder system of claim 1, wherein the powder system remains stable at 25° C./60% relative humidity for at least 2 years.

8. An oral pharmaceutical suspension, comprising water and a pharmaceutically effective amount of a storage-stable omeprazole powder system of claim 1 dispersed in the water, and wherein the suspension contains sodium and potassium at a ratio of from about 1:2.6 to about 1:3.4 by weight.

9. The oral pharmaceutical suspension of claim 8, wherein about 1 ml of the suspension contains from about 1 mg to about 10 mg of omeprazole, or the pharmaceutically acceptable salt thereof.

10. The oral pharmaceutical suspension of claim 8, wherein the first and second buffering agents together provide a buffering capacity of about 2 mEq per ml of the suspension.

11. The oral pharmaceutical suspension of claim 8, wherein the suspension is provided in a drug delivery device suitable for multi-dose administration of omeprazole.

12. A method of inhibiting gastric acid secretion, comprising administering to a subject in need thereof an effective amount of the oral pharmaceutical suspension of claim 8.

13. The method of claim 12, wherein the subject is a child.

14. A method of preparing an oral pharmaceutical suspension, comprising combining (i) a first powder mixture comprising (a) a therapeutically effective amount of omeprazole, or a pharmaceutically acceptable salt thereof, (b) sodium alginate, and (c) a first buffering agent; with (ii) a second powder mixture comprising sodium alginate and a second buffering agent; to obtain a combined mixture, wherein the combined mixture contains sodium and potassium at a ratio of from about 1:2.6 to about 1:3.4 by weight; and adding water to the combined mixture.

15. A method of inhibiting gastric acid secretion, comprising administering to a subject in need thereof an effective amount of an oral pharmaceutical suspension comprising water, a pharmaceutically effective amount of omeprazole, or a pharmaceutically acceptable salt thereof, and sodium alginate dispersed in the water, and a first and a second buffering agent, wherein the suspension contains sodium and potassium at a ratio of from about 1:2.6 to about 1:3.4 by weight; and wherein the oral pharmaceutical suspension is prepared as claimed in claim 14.

16. The oral pharmaceutical suspension of claim 8, wherein the suspension remains stable for at least one month at 2° C.-8° C. after constitution with water.

17. A method of administering an oral pharmaceutical suspension to a subject in need of inhibition of gastric acid secretion, said method comprising 1) preparing an oral pharmaceutical suspension, comprising combining (i) a first powder mixture comprising (a) a therapeutically effective amount of omeprazole, or a pharmaceutically acceptable salt thereof, (b) sodium alginate, and (c) a first buffering agent; with (ii) a second powder mixture comprising sodium alginate and a second buffering agent; to obtain a combined mixture, wherein the combined mixture contains sodium and potassium at a ratio of from about 1:2.6 to about 1:3.4 by weight; and adding water to the combined mixture; and 2) administering to the subject in need thereof an effective amount of the oral pharmaceutical suspension.

18. The method of claim 17, wherein the subject is a child.

19. The storage-stable omeprazole powder system of claim 1, wherein the first and second buffering agents together provide a buffering capacity of about 2 mEq/ml dose of constituted powder with water.

20. The storage-stable omeprazole powder system of claim 1, wherein the first and second buffering agents are each independently selected from the group consisting of alkali metal or alkaline earth metal carbonates, bicarbonates, phosphates, citrates, borates, acetates, phthalates, tartrates, succinates, and mixtures thereof.

21. The storage-stable omeprazole powder system of claim 4, wherein the first buffering agent is sodium bicarbonate.

22. The storage-stable omeprazole powder system of claim 4, wherein the second buffering agent is a mixture of sodium bicarbonate and potassium bicarbonate.

23. The storage-stable omeprazole powder system of claim 1, wherein the first powder mixture and the second powder mixture together comprise sodium bicarbonate and potassium bicarbonate at a ratio of about 1:2.7 by weight.

24. The storage-stable omeprazole powder system of claim 5, wherein the drug delivery device comprises a first chamber comprising the first powder mixture and a second chamber comprising the second powder mixture.

25. The storage-stable omeprazole powder system of claim 24, wherein the drug delivery device further comprises a means for releasing the first powder mixture into the second chamber without removing the cap from the drug delivery device.

26. The oral pharmaceutical suspension of claim 9, wherein about 1 ml of the suspension contains about 2 mg or about 4 mg of omeprazole, or the pharmaceutically acceptable salt thereof.

27. The oral pharmaceutical suspension of claim 8, wherein the sodium and potassium are present at a ratio of about 1:3.2 by weight.

* * * * *